(12) United States Patent
Bagwan et al.

(10) Patent No.: US 11,571,189 B2
(45) Date of Patent: Feb. 7, 2023

(54) DEVICES AND METHODS FOR EXTRACTION AND COLLECTION OF TISSUE SAMPLES

(71) Applicant: SECRETARY, DEPARTMENT OF BIOTECHNOLOGY, New Delhi (IN)

(72) Inventors: Siraj Shoukat Bagwan, Bangalore (IN); Praveen Deelip Nalawade, Belgaum (IN); Rasheed Ahmed, Bangalore (IN); Premanand Sugumaran, Bangalore (IN)

(73) Assignee: SECRETARY, DEPARTMENT OF BIOTECHNOLOGY, New Delhi (IN)

( * ) Notice: Subject to any disclaimer, the term of this patent is extended or adjusted under 35 U.S.C. 154(b) by 915 days.

(21) Appl. No.: 16/467,462

(22) PCT Filed: Dec. 7, 2017

(86) PCT No.: PCT/IN2017/050577
§ 371 (c)(1),
(2) Date: Jun. 6, 2019

(87) PCT Pub. No.: WO2018/104964
PCT Pub. Date: Jun. 14, 2018

(65) Prior Publication Data
US 2019/0321015 A1  Oct. 24, 2019

(30) Foreign Application Priority Data

Dec. 7, 2016 (IN) .............................. 201611041748

(51) Int. Cl.
*A61B 10/02* (2006.01)
*A61B 10/00* (2006.01)

(52) U.S. Cl.
CPC ...... *A61B 10/0283* (2013.01); *A61B 10/0096* (2013.01)

(58) Field of Classification Search
CPC ............ A61B 10/0283; A61B 10/0096; A61B 2010/0208; A61B 2010/0225; A61B 10/0275; A61B 10/0233
See application file for complete search history.

(56) References Cited

U.S. PATENT DOCUMENTS 8,485,989 B2 * 7/2013 Videbaek ........... A61B 10/0275
600/568
2010/0317998 A1 * 12/2010 Hibner ............... A61B 10/0275
600/567

(Continued)

FOREIGN PATENT DOCUMENTS

WO  WO 2014/028366 A1    2/2014
WO  WO-2014091502 A1 *   6/2014  ......... A61B 10/0233

(Continued)

OTHER PUBLICATIONS

International Application Status Report, dated Jun. 5, 2019, in International Patent Application No. PCT/IN2017/050577.

(Continued)

*Primary Examiner* — Rene T Towa
(74) *Attorney, Agent, or Firm* — Knobbe, Martens, Olson & Bear LLP

(57) ABSTRACT

A device including a probe unit and a driver unit for tissue extraction and sample collection is disclosed. The probe unit includes an injection unit, a driving mechanism, a filtering mechanism and a tissue sample container. The injection unit includes a needle actuated by a prime-mover and the driving mechanism, which drives the needle into the subject for extraction of tissue sample. The tissue extraction is performed by a rotational motion of the needle and pressure. The pressure is provided by a pressure subsystem in the lumen of the needle and the tissue is collected in the tissue sample container. The amount of pressure applied is con- (Continued)

trolled by a control subsystem based on the organ specific requirement.

8 Claims, 14 Drawing Sheets

(56) References Cited

U.S. PATENT DOCUMENTS

| | | |
|---|---|---|
| 2011/0201963 A1 | 8/2011 | Deupree |
| 2011/0208086 A1* | 8/2011 | Hibner ............... A61B 10/0275 600/566 |
| 2012/0109007 A1* | 5/2012 | Rhad ................. A61B 10/0096 600/567 |
| 2013/0041254 A1* | 2/2013 | Hagy .................. A61B 8/4411 600/424 |
| 2016/0262733 A1* | 9/2016 | Schlarb .............. A61B 10/0275 |
| 2017/0242980 A1* | 8/2017 | Barrington ............ G16H 10/40 |

FOREIGN PATENT DOCUMENTS

| | | |
|---|---|---|
| WO | WO 2014/182488 A1 | 11/2014 |
| WO | WO 2015/010012 A1 | 1/2015 |

OTHER PUBLICATIONS

International Search Report and Written Opinion, dated Feb. 27, 2018, in International Patent Application No. PCT/IN2017/050577.

\* cited by examiner

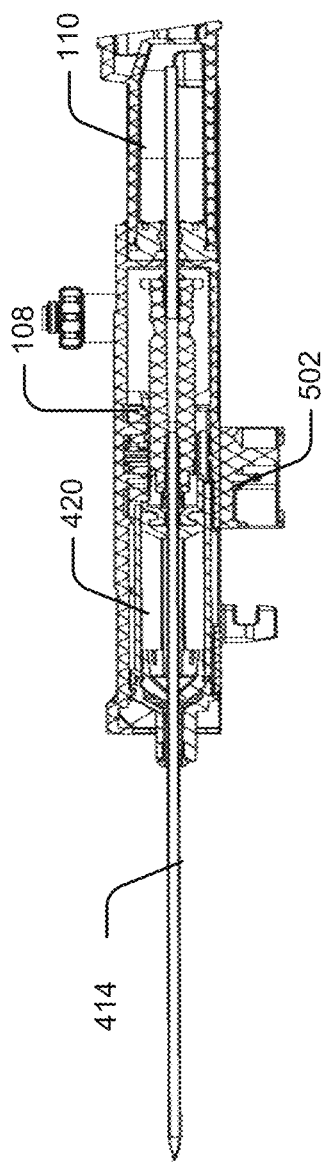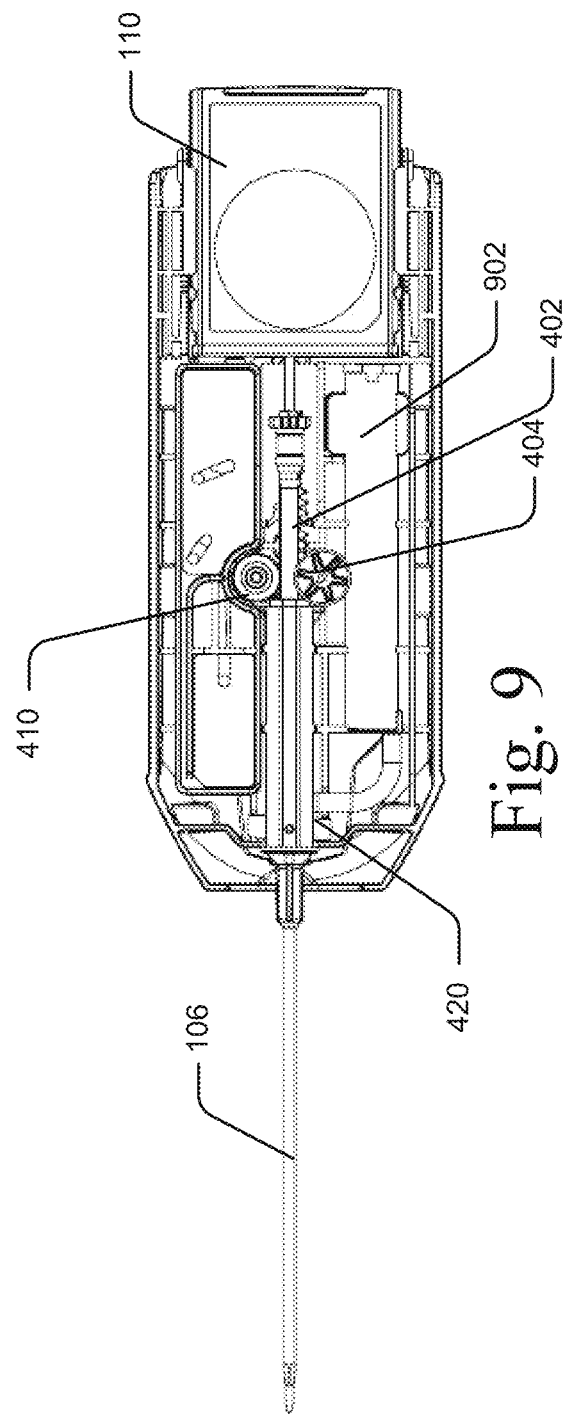

DEVICES AND METHODS FOR EXTRACTION AND COLLECTION OF TISSUE SAMPLES

PRIORITY AND CROSS REFERENCE TO RELATED APPLICATIONS

This application is the U.S. National Stage Application under 35 U.S.C. § 371 of International Application No. PCT/IN2017/050577, filed Dec. 7, 2017, designating the U.S. and published in English as WO 2018/104964 A1 on Jun. 14, 2018, which claims the benefit of Indian Patent Application No. IN 201611041748, filed Dec. 7, 2016. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present subject matter, in general, relates to soft tissue biopsy, and in particular, to a device for extraction and collection of tissue samples.

BACKGROUND

A biopsy procedure involves extraction of tissue samples from body tissues to diagnose various health conditions, such as diseases related to liver, prostate, breast, kidney, lungs, etc., and to identify infectious tissues, such as malignant or benign tumours in the body of a subject. To extract the tissue sample, a surgeon or a doctor first identifies a position of the biopsy region based on physical palpation, auditory auscultation, visual imaging, or a combination of these techniques.

Further, a needle in a biopsy apparatus is moved towards the biopsy region to extract the body tissue samples. Different procedures of biopsies are used for different body parts or the affected tissue area. For example, incisional or needle biopsy procedure may involve a special needle, such as Menghini aspiration needle, Tru-cut needle or BioPince needle, which are used to extract tissue or cells from a body area, such as muscles, bones, and organs, such as liver or lungs.

SUMMARY

The present disclosure is related to devices and methods for extraction and collection of tissue samples.

BRIEF DESCRIPTION OF THE DRAWINGS

A detailed description is provided with reference to the accompanying figures. In the figures, the left-most digit(s) of a reference number identifies the figure in which the reference number first appears. The same numbers are used throughout the drawings to reference like features and components.

FIG. 8 illustrates sectional side view of the probe unit, according to an embodiment of the present subject matter.

FIG. 9 illustrates bottom view of the probe unit with an auxiliary container, according to an embodiment of the present subject matter.

DETAILED DESCRIPTION

Figure 1:
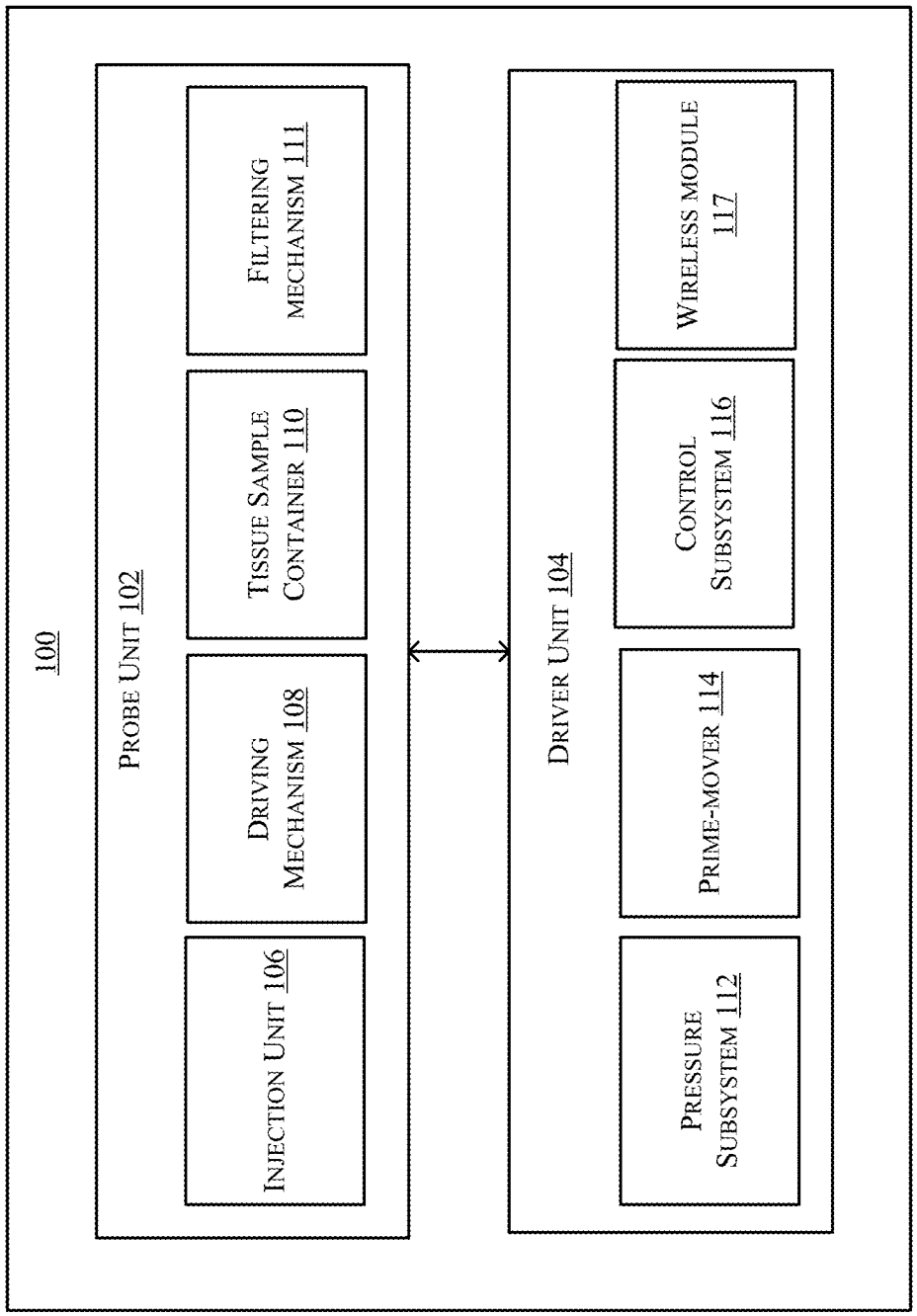
FIG. 1 illustrates a block diagram of a device for biopsy, according to an embodiment of the present subject matter.

The present subject matter relates to a device for extraction and collection of tissue sample.

Generally, aspiration needle biopsy procedures are performed to obtain a core tissue sample. Aspiration needle biopsy involves inserting a needle into the soft tissue. Quality and quantity of sample obtained depend on the amount of negative pressure applied as well as the swift movement of the needle. Since both the parameters are manually controlled, the sample quality and quantity are determined by the skill of the operator to a great extent.

Further, in aspiration needle biopsy, only a linear movement of the needle is provided. As there is only a linear movement involved, the tissue may not shear completely at a distal end of the needle resulting in a fragmented tissue sample.

In another technique, called the Tru-Cut technique, there is rapid advancement of stylet followed by cutting cannula to obtain the tissue sample. This may lead to crush artefacts where the tissue is compressed, thus deteriorating the diagnostic quality of the sample. In some cases, quantity of sample maybe inadequate as the thickness of the sample may be limited by a notch and an inner diameter of a cannula associated with the needle. In this technique, the needle is inserted into the patient's body till it reaches the organ surface and then the stylet is advanced to obtain a sample. This length of insertion of the needle before taking a sample is more often than not based on the physician's expertise and determines largely the diagnostic value of the sample. The biopsy procedures, therefore, have many variables and require considerable amount of skills from the medical practitioners. Often, the procedure may be repeated if the sample is inadequate or unsuitable for diagnosis, which further increases the clinical risk.

Further, in the conventional biopsy devices, the practitioners are exposed to risks of contracting infectious diseases such as Hepatitis, Blood borne diseases, etc., while handling the sample, or due to accidental needle prick or careless handling of the device. Additionally, the subject is also at a risk of contracting infections if the needle assembly prescribed for single use is used repeatedly on multiple patients in contravention to safety guidelines.

In most cases, the biopsy devices used by medical practitioners have complex spring-loaded mechanisms for linear actuation and retrieval of the sample. Moreover, in the vacuum-assisted biopsy systems, pressure pumps and pressure storage containers are located separately and pressure is transferred to the biopsy device via external conduits as and when required, which limits the manoeuvrability and portability of the biopsy device. Further, in some configurations with internal pressure pump, stabilizing the pressure generated by the pressure pump may take considerable amount of procedure time, and also cause vibrations in the device during the procedure, adding to the discomfort and anxiety of the patient.

Additionally, different organs may need different amount of negative pressure at the needle end to extract the tissue. This could further increase the procedural time. Furthermore, in case of loosely tethered, soft-tissue organs, such as liver, kidney, etc., localized internal displacement of target tissue as a result of respiration or external movement from patient instability, may cause further clinical complications such as internal bleeding and laceration during sample extraction. Further, for performing proper examination of tissue samples, it is also desirable to extract fully intact, clean core samples that have not been crushed or fragmented by devices penetrating into tissue.

Therefore, there is a need for a biopsy device that reduces physician skill dependency by providing automated and precise control of procedural parameters for performing the organ specific biopsy procedures. Tissue sample quality can be improved by providing appropriate negative pressure for complete separation of the tissue sample from the surrounding tissue. The biopsy device should also limit the usage of the needle assembly for one time use and incorporate features for extracting, filtering, and storing, the tissue sample while overcoming the abovementioned disadvantages with minimum procedural time.

The present subject matter relates to a device for biopsy. The device provides automated extraction and collection of tissue samples. The device includes a probe unit and a driver unit. The 'driver unit' hereby refers to the handheld portion of the device that includes a pressure subsystem, a prime-mover, control subsystem and a wireless module. The 'probe unit' hereby refers to the unit that may be detachably mounted on the driver unit and disposed after single use. The probe unit includes an injection unit, a tissue sample container, a filtering mechanism and a driving mechanism. The driving mechanism of the probe unit is coupled to the driver unit.

The injection unit includes a needle for biopsy. The driving mechanism is for actuation of the injection unit. The driving mechanism includes a shaft member. The needle is fixedly attached in the shaft member. In an embodiment, the needle body may be concentrically attached in the shaft member, which can be actuated by the driving mechanism for bi-directional sequential movement to perform the biopsy procedure. The driving mechanism is to advance the shaft member and retract the shaft member in a linear direction and to produce a rotational motion of the shaft member.

The injection unit may include a cannula which can be inserted into a subject for tissue extraction. The needle as described in WO2014091502A1 comprises a distal end, a proximal end, and a lumen for extracting tissue samples of organs. The distal end of the needle is concentrically covered by the cannula and the proximal end is housed in a tissue sample container included in the probe unit. An annular space may be provided between the cannula and the needle.

The driving mechanism includes a driver gear, a transmission gear, a stability gear, at least one driven gear, and a gear rack positioned on the shaft member. The driver gear is engaged to the transmission gear, the gear rack, the stability gear, and a drive shaft of a prime-mover. The prime-mover may be fixedly attached in a mounting element, which is positioned in the driver unit. The prime-mover is for actuation of the needle by actuating the driving mechanism for advancing, retracting, and rotating the needle. In an embodiment, the prime-mover may be a motor that produces a rotational motion of the drive shaft for driving the driver gear, which further drives the transmission gear and the at least one driven gear. The driver gear also drives the gear rack to produce a linear motion of the shaft member. In operation, the linear motion of the shaft member projects the distal end of the needle through the cannula and inserts it into the target tissue for cutting and extracting the sample.

Further, a "needle depth adjuster" as referred to earlier may be attached at the distal end of the driver unit below the injection unit. The needle depth adjuster has a circular disc at one end and locking arm at the other end. The needle depth adjuster may be extendable to a certain length and locked to prevent or limit undesired length of needle insertion. When the insertion of the needle and the cannula is performed, the circular disc rests externally on the patient's skin to provide a stable operation of the device and also to isolate the device from the patient.

In an embodiment, the needle depth adjuster comprises an aligning unit for ensuring that the needle can align within any other device, such as an imaging device, used during tissue extraction to visualize the needle with reference to kidney and lungs prior to taking biopsy.

In another embodiment, the needle depth adjuster is provided with a semi-circular flap that along with the cannula may be used for determining the site to enable tissue marker delivery for future reference as in case of a breast biopsy.

Further, the shaft member may include a transitional gear, which engages with the transmission gear due to the linear motion of the shaft member. The engaging of the transmission gear and the transitional gear produces a rotational motion of the shaft member. The rotational motion of the shaft member rotates the needle. The needle, consequentially, separates the tissue sample at the distal end inside the organ, which is then extracted in the lumen.

Further, when the shaft member completes rotation by a predetermined angle, the gear rack reengages with the at least one driven gear. This engagement converts the rotational motion of the shaft member to linear motion and the shaft member retracts to its original position. The needle travels back through the cannula and retracts to its original position.

In one embodiment, a fluid, such as a haemostatic agent, may be provided through the cannula during the extraction of the tissue sample as described in WO2015025328A1. The fluid may be stored in a container, and the flow of the fluid may be actuated by the driving mechanism.

Further, for biopsy a pressure is applied to the proximal end of the needle located in a tissue sample container, by the pressure subsystem. The pressure subsystem is coupled to the probe unit. The pressure subsystem includes a pressure pump to supply negative pressure to the probe unit for biopsy. The pressure subsystem, which is positioned in the driver unit may be connected to the probe unit by an interfacing element, such as a vacuum cup or vacuum seal.

The pressure subsystem includes a pressure storage chamber to store the pressure supplied by the pressure pump. The pressure subsystem may include a pressure sensor for measuring the pre-programmed pressure in a pressure storage chamber. Based on the measurement, the control subsystem of the driver unit is to control the pressure subsystem to provide varying amount of pressure for biopsy. In an embodiment, the control subsystem may control the pressure pump to increase or decrease the pressure in the pressure storage chamber. Further, in another embodiment, the control subsystem may control a solenoid valve of the pressure subsystem for applying the pressure instantaneously, reducing time consumption, and for maintaining the pressure applied in the needle.

When negative pressure is applied, the biopsy device assists in prolapse of the tissue and the tissue extraction, which enables a continuous length of tissue to be cored into the lumen. The extracted tissue accumulated in the lumen travels from the distal end to the proximal end due to the negative pressure. In an embodiment, the tissue may be transferred to the tissue sample container provided in the probe unit which may then be detached from the probe unit for examination, storage, and/or transportation of the tissue sample. In another embodiment, a new tissue sample container may be installed in the probe unit for collecting another sample from the same patient. Further, the probe unit may be detached and disposed off after the extraction and collection of the tissue sample(s) from the patient. Additionally, the needle depth adjuster may also be detached from the driver unit and disposed off after the procedure. The probe unit and driver unit can comprise other components, for example, a filtering mechanism and a wireless module, respectively.

Therefore, the present subject matter provides an automated, portable, and adaptive biopsy device. The biopsy device assists the operator in implementing the biopsy procedure by a pre-determined, controlled linear and rotational movement of the needle supplemented with an appropriate amount of pressure for extraction of tissue sample. The device reduces the risk of infection by accidental needle prick injury or improper sample handling. Further, precise, closed loop, and controlled needle insertion helps to mitigate the shortcomings of manual operations, such as poor quality or inadequate quantity or size of the sample, and the possibility of damage to the tissue extracted for examination by fragmentation or during subsequent manual handling. Additionally, the automated device is easy to handle and minimizes the possibility of surgical complications occurring due to use of biopsy devices that are highly skill dependent.

FIG. 1 illustrates a block diagram of a device 100 for biopsy, hereinafter called biopsy device 100, according to an embodiment of the present subject matter. The biopsy device 100 includes a probe unit 102 and a driver unit 104. The probe unit 102 may include an injection unit 106, a driving mechanism 108, a tissue sample container 110, and a filtering mechanism 111. The driver unit 104 may include a pressure subsystem 112, a prime-mover 114, a control subsystem 116, and a wireless module 117. The probe unit 102 may be detachably mounted on the driver unit 104 and disposed off after use.

The injection unit 106 includes a needle and a cannula, which can be inserted into a subject for tissue extraction. The needle comprises a distal end, a proximal end, and a lumen for extracting tissue samples of organs. The distal end of the needle is concentrically covered by the cannula and the proximal end is housed in the tissue sample container 110. Further, the needle body may be concentrically attached in a hollow shaft member, which can be actuated by the driving mechanism 108.

The driving mechanism 108 includes a driver gear, a transmission gear, a stability gear, at least one driven gear, and a gear rack positioned on the shaft member. The driver gear is engaged to the transmission gear, the gear rack, the stability gear, and a drive shaft of a prime-mover 114. The prime-mover 114 is fixedly attached in a mounting element, which is positioned in the driver unit 104. The prime-mover 114 may be a motor that produces a rotational motion of the drive shaft for driving the driver gear. The driver gear further drives the transmission gear and the at least one driven gear. The driver gear also drives the gear rack to produce a linear motion of the shaft member to advance the shaft member in a linear direction. The linear motion of the shaft member projects the distal end of the needle through the cannula and inserts it into the organ.

Further, as will be discussed in detail with reference to subsequent figures, when the shaft member completes rotation by a predetermined angle, for example 180°, a transitional gear mounted on the proximal end of the shaft member engages with the transmission gear due to the linear motion of the shaft member. The engaging of the transmission gear and the transitional gear produces a rotational motion of the shaft member. Therefore, the transmission gear is to drive the transitional gear to produce the rotational motion of the shaft member. The rotational motion of the shaft member rotates the needle and the needle extracts a part of the tissue of the organ, which gets accumulated in the needle lumen.

Further, when the shaft member completes rotation by a predetermined angle, for example 180°, the gear rack engages with the at least one driven gear. The gear rack is to drive the at least one driven gear to retract the shaft member in the linear direction by converting the rotational motion of the shaft member to the linear motion. The shaft member, therefore, retracts to its original position. The needle travels back through the cannula and retracts to its original position.

In one embodiment, a fluid, such as a haemostatic agent, may be provided through the cannula during the extraction of the tissue sample. The fluid may be stored in a container, and flow of the fluid may be actuated by the driving mechanism, as will be discussed later.

Further, a pressure is applied to the proximal end of the needle located in the tissue sample container 110 by a pressure subsystem 112. A negative pressure may be applied to collect the tissue sample in the tissue sample container 110. In another embodiment, when the tissue sample container 110 is external to the device 100, the negative pressure may be applied to collect the tissue sample in the needle. Consequently, a positive pressure is applied to transfer the tissue sample in the external container. The pressure subsystem 112 may be connected to the probe unit 102 by an interfacing element, such as a vacuum cup or vacuum seal.

During normal operation, the extracted tissue accumulated in the lumen of the needle travels from the distal end to the proximal end due to the negative pressure. The negative pressure assists in prolapse of the tissue and the tissue extraction, which enables a continuous length of tissue to be cored into the lumen. In an embodiment, the tissue extracted may be filtered, for example, by the filtering mechanism 111 as will be explained later with reference to FIG. 10A and FIG. 10B.

At the proximal end, the tissue may be collected in the tissue sample container 110 which may then be detached from the probe unit 102 for examination, storage, and/or transportation of the tissue sample. In one embodiment, a new tissue sample container may be installed in the probe unit 102 for collecting another sample from the patient. Further, the probe unit 102 may be disposed off after the extraction and collection of the tissue sample from one patient and a different probe unit may be used for the next patient. Thus, while the driver unit 104 may be commonly used with different probe units for different patients and different organ biopsies, the probe units themselves would be detached and changed for every procedure, thus eliminating the risk of cross-infections. Accordingly, the biopsy device 100 is adapted such that that the driver unit 104 does not come in contact with any body fluids during the biopsy procedure and can be easily cleaned and serviced.

Figure 2A:
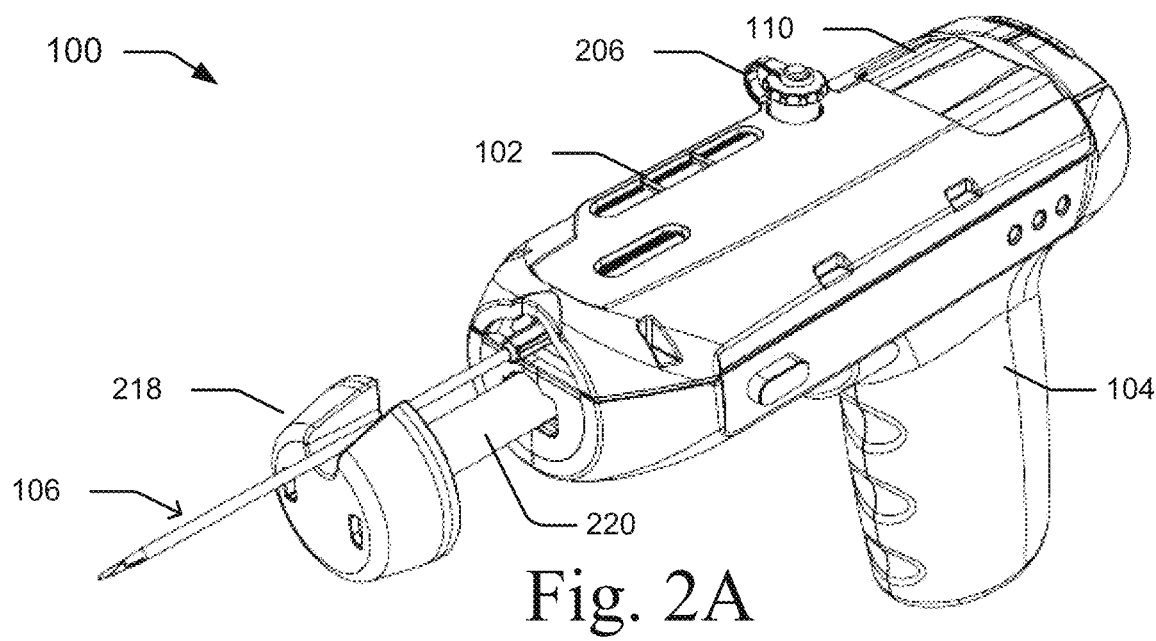
FIGS. 2A and 2B illustrate assembled and exploded views of the biopsy device, according to an embodiment of the present subject matter.
Figure 2B:
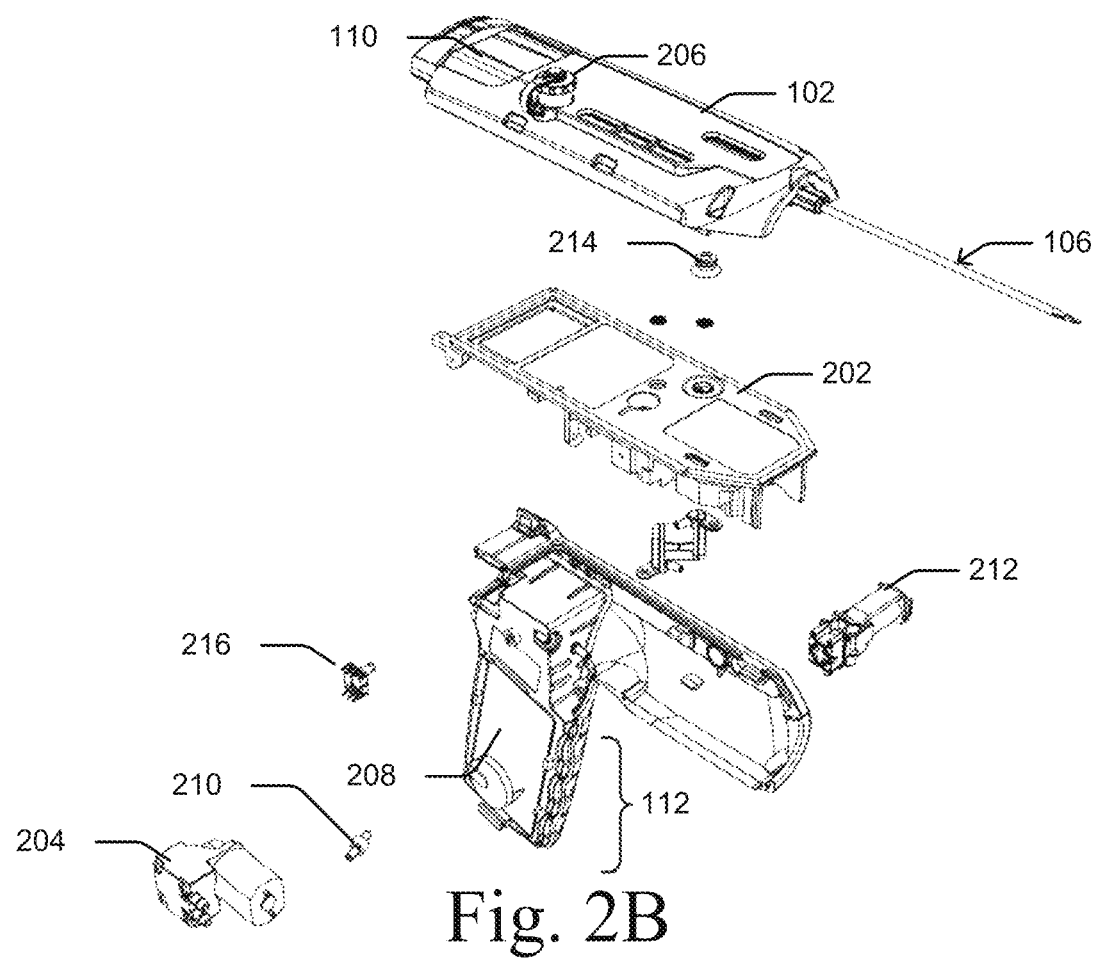

FIGS. 2A and 2B illustrate assembled and exploded views of the biopsy device 100 according to an embodiment of the present subject matter. In one example, the biopsy device 100 may be used for biopsy of organs, such as liver. The biopsy device 100 includes the probe unit 102 and the driver unit 104 such that, the biopsy device 100 can be hand held by a user, such as a doctor.

The probe unit 102 may be mounted on the driver unit 104 and may be detached and disposed off after use. The probe unit 102 includes injection unit 106, driving mechanism (not shown in this figure), and the tissue sample container 110. The driver unit 104 primarily includes the pressure subsystem 112 (FIG. 2B), the control subsystem and a prime-mover (both not shown in this figure). Further, the driver unit 104 includes the mounting element 202 for mounting and enclosing the prime-mover 114 and a pressure pump 204 of the pressure subsystem 112.

The injection unit 106 includes a needle, which may be fixedly attached inside a hollow shaft member and actuated by the driving mechanism (not shown in this figure). In one embodiment, the injection unit 106 may include an outer casing to cover the injection unit. The outer casing may prevent accidental prick of the needle during the handling of the probe unit 102. The driving mechanism is powered by a prime-mover (not shown in this figure) for driving the needle. The driving mechanism includes various components, as will be discussed later.

In one embodiment, the probe unit 102 includes a container (not shown in figure) for providing fluid to the region where the needle extracts tissue sample to prevent bleeding. The fluid, such as medicament, may be filled in the container through a cap 206 placed on top of the probe unit 102. The medicament may be provided into the subject through the cannula and may be injected using the driving mechanism, as will be discussed later.

Further, the pressure subsystem 112 includes a pressure storage chamber 208, which is provided at bottom portion of the driver unit 104 for storing pressure such that, pressure from the pressure storage chamber 208 is readily available for utilization. The pressure may be generated by the pressure pump 204, which is powered by a power source (not shown in this figure). In one embodiment, the power source is at least one of lithium ion battery, lithium polymer, rechargeable battery, solar powered battery, or any other power source, which serves the purpose.

A check valve 210 may be coupled between the pressure storage chamber 208 and the pressure pump 204 to prevent reverse flow of the pressure stored in the pressure storage chamber 208 to the pressure pump 204. Further, solenoid valve 212 may be coupled to the pressure storage chamber 208 to control the pressure provided from the pressure storage chamber 208 to the probe unit 102 for biopsy. The pressure subsystem 112 may include an interfacing element 214. The solenoid valve 212 allows stored pressure into interfacing element 214 and controls generated pressure based on the requirement of the user.

In one embodiment, the pressure storage chamber 208 is equipped with a pressure sensor 216 for indicating the amount of pressure available for use to the control subsystem. For example, the amount of pressure available may be displayed in a display unit (not shown in this figure), which may be positioned on the driver unit 104.

In one embodiment, a needle depth adjuster 218 may be attached at the distal end of the injection unit 106. The needle depth adjuster 218 may be extendable to a certain length and locked to prevent movement. The needle depth adjuster 218 rests on the patient's skin when the injection unit 106 is inserted in the subject and this provides a stable operation of the biopsy device 100 and also isolating the biopsy device 100 from the patient.

The needle depth adjuster 218 has a circular disc at a first end and locking arm 220 at a second end. The locking arm 220 is to lock the driver unit 104 at a locking position to provide stability to the device during operation. For example, a locking position may be decided by extending or retracting the locking arm 220 based on a measurement received from an ultrasound device. The ultrasound device may be used for detecting the proximity of organ to the skin and accordingly the locking arm 220 may be extended or retracted.

In one embodiment, the locking arm 220 of the needle depth adjuster 218 has tooth-like structure at one end that locks into the grooves present in the driver unit 104. In an embodiment, the locking arm 220 is to control a length of needle pierced into the patient's body. In another embodiment, the locking arm 220 may lock with the driver unit 104 using a ratchet mechanism. Further, a magnet (not shown in this figure) may be provided on the locking arm 220, which may be detected by a plurality of magnetic sensors present on PCBs in the driver unit 104. Therefore, the length of the needle is detected based on a position of the magnet by the plurality of magnetic sensors.

Figure 2C:
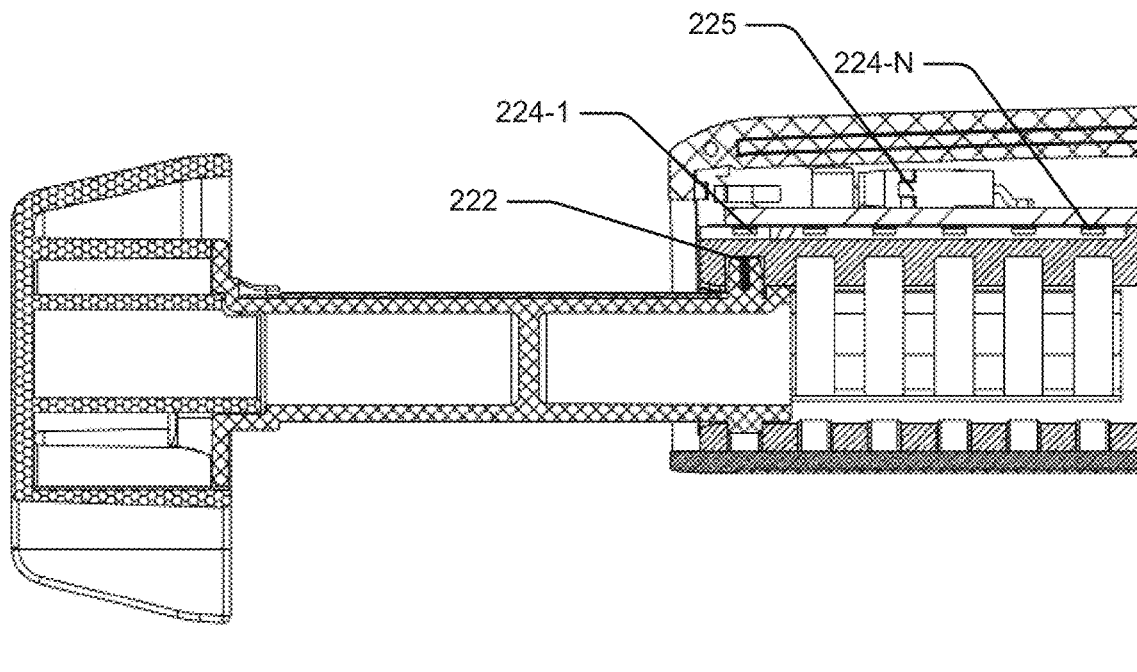
FIG. 2C illustrates a magnet on a locking arm, according to an embodiment of the present subject matter.

FIG. 2C illustrates a magnet 222 on the locking arm 220, in accordance with an embodiment of the present subject matter. The magnet 222 may be detected by the sensors 224-1, 224-2, . . . , 224-N. This enables recording the length of needle inserted into the subject based on the position of the sensor that detects the magnet 222 on the locking arm 220. Further, the control subsystem 116 may be provided inputs regarding whether the needle depth adjuster device 218 has been pressed against the subject from the stopper switch 225 and indicate the same to the user. Further, the device may be configured and designed to incorporate additional or alternate components, elements, or parts, so as to perform biopsy on various organs, such as kidneys, prostate, breast etc., as discussed later. In addition, the sequence of operation of the devices used for the tissue extraction and collection from different organs may be differently implemented.

Figure 2D:
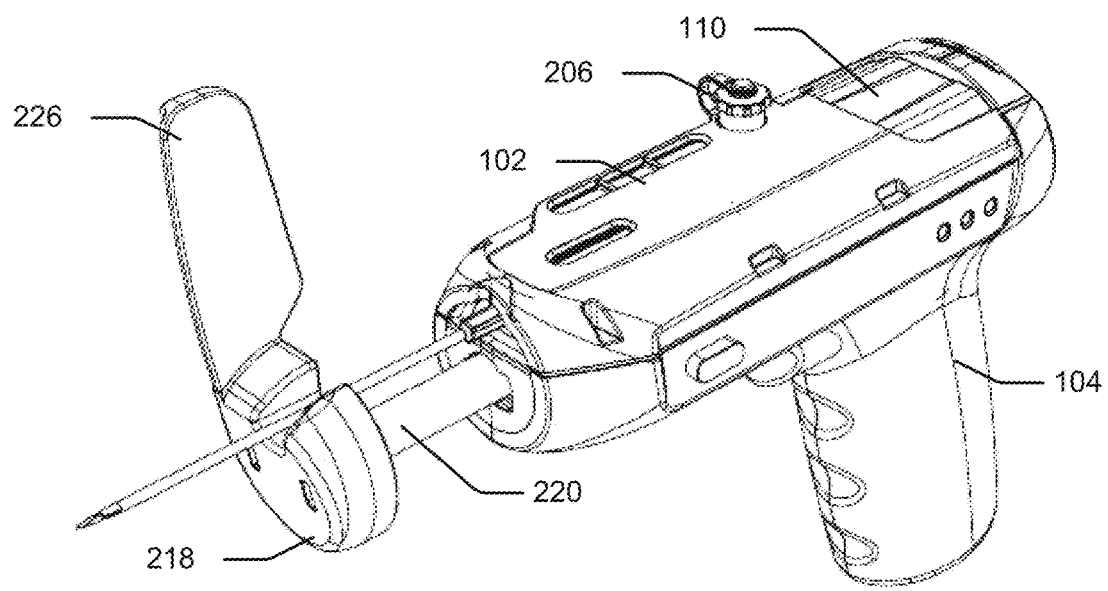
FIG. 2D illustrates assembled view of the biopsy device, according to an embodiment of the present subject matter.

FIG. 2D illustrates a biopsy device for extracting and collecting tissue samples from kidneys and lungs, in accordance with an implementation of the present subject matter. The needle depth adjuster 218 includes an aligning unit 226 for ensuring that the needle can align within any other device, such as an imaging device, used during tissue extraction to visualise the needle with reference to kidney and lungs prior to taking biopsy. For example, the aligning unit 226 enables/assist the user to efficiently align an ultrasound probe with the needle to enable accurate viewing of the needle insertion path in the ultrasound imaging. Hence, the user can perform the tissue extraction at the appropriate location. The probe unit 102 may also include an auxiliary container (not shown in figure) for providing an auxiliary fluid. The auxiliary fluid acts as a reservoir and enables refilling of the container for multiple uses. In another embodiment, it could be one of the two components that need to be mixed prior to delivery, the other being the fluid contained in the container. The auxiliary fluid may be provided through the cap 206 present on the probe unit 102. In one embodiment, for example, in case of lung biopsy, an annular space provided between the needle and the cannula may be sealed to prevent pneumothorax.

Figure 2E:
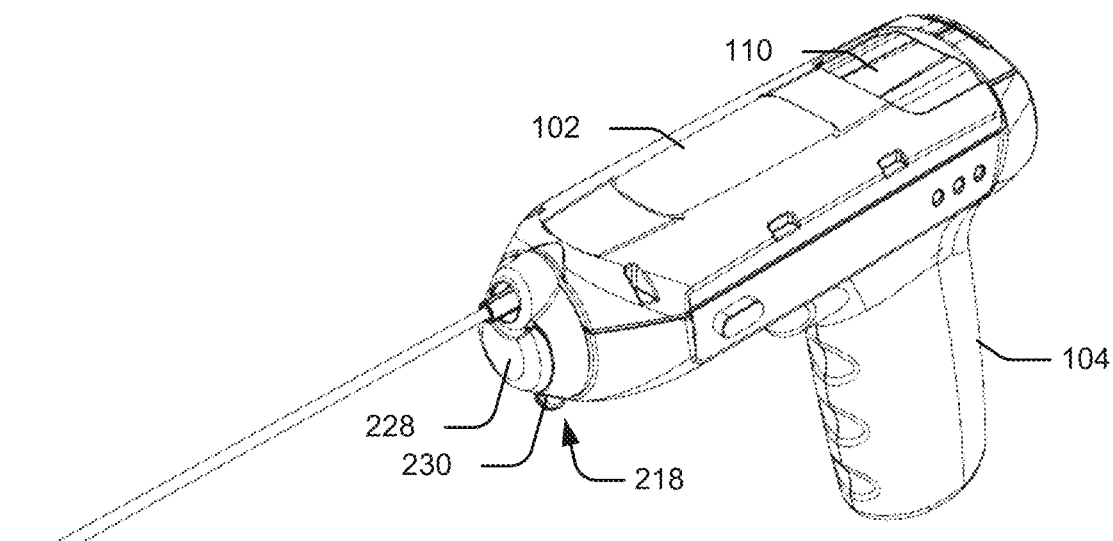
FIG. 2E illustrates assembled view of the biopsy device, according to an embodiment of the present subject matter.

Further, FIG. 2E illustrates a device for extracting and collecting breast tissue samples. In breast biopsy, there is no requirement for controlling the depth of needle inserted, therefore, the needle depth adjuster 218 may be adapted for a different function, for example, for enabling tissue marker delivery. Once inserted into the target organ, the tissue marker may be used for locating biopsy site for future reference. In this embodiment, the needle depth adjuster 218 is divided into two parts—the central part 228, which may be locked with the driver unit, and a semi-circular flap 230 coupled to the central part 228 having an open-close configuration, which may be provided on the driver unit 104. The semi-circular flap 230 is closed during the biopsy. After completion of biopsy, the flap 230 may be opened.

Figure 2F:
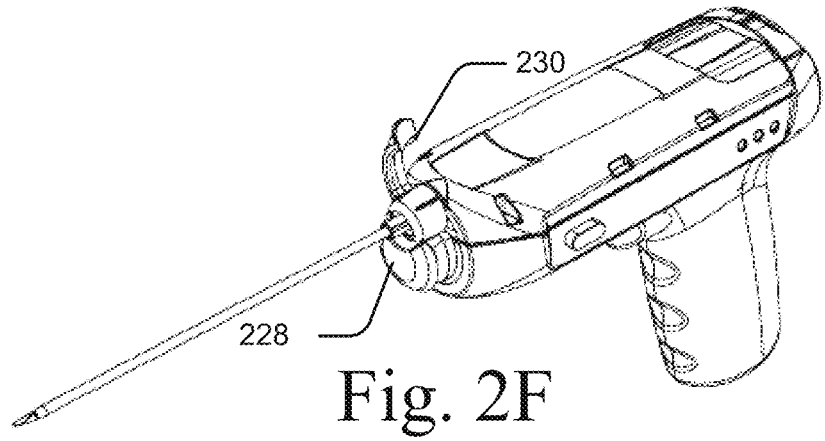
FIG. 2F illustrates assembled view of the biopsy device, according to an embodiment of the present subject matter.

FIG. 2F illustrates the flap 230 in the open position. Upon opening the flap 230, the needle can be withdrawn. Further, the flap 230 along with the cannula may be used for determining the site to enable tissue marker delivery for future reference.

Figure 2G:
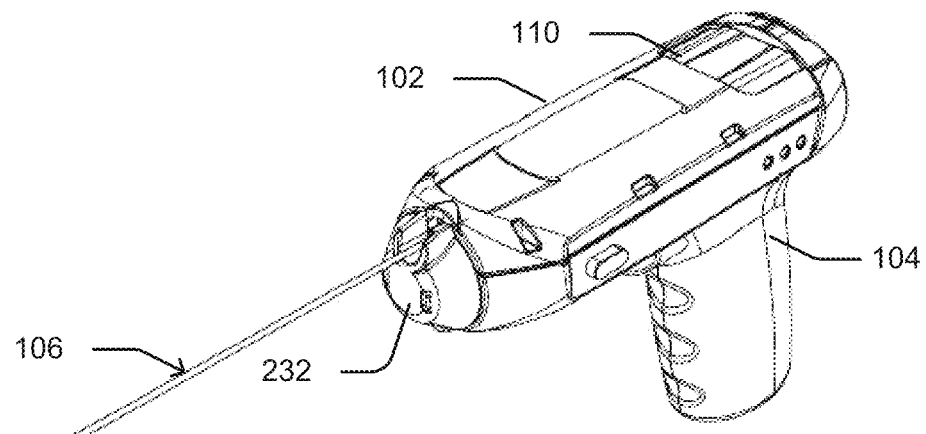
FIG. 2G illustrates assembled view of the biopsy device, according to an embodiment of the present subject matter.

In another embodiment, the biopsy device 100 may not include the needle depth adjuster. FIG. 2G illustrates a device for performing biopsy for soft tissues, such as prostate tissue, which may not need a needle depth adjuster. Accordingly, a needle depth adjuster-like cover 232 may be provided along with probe unit 102.

Figure 3:
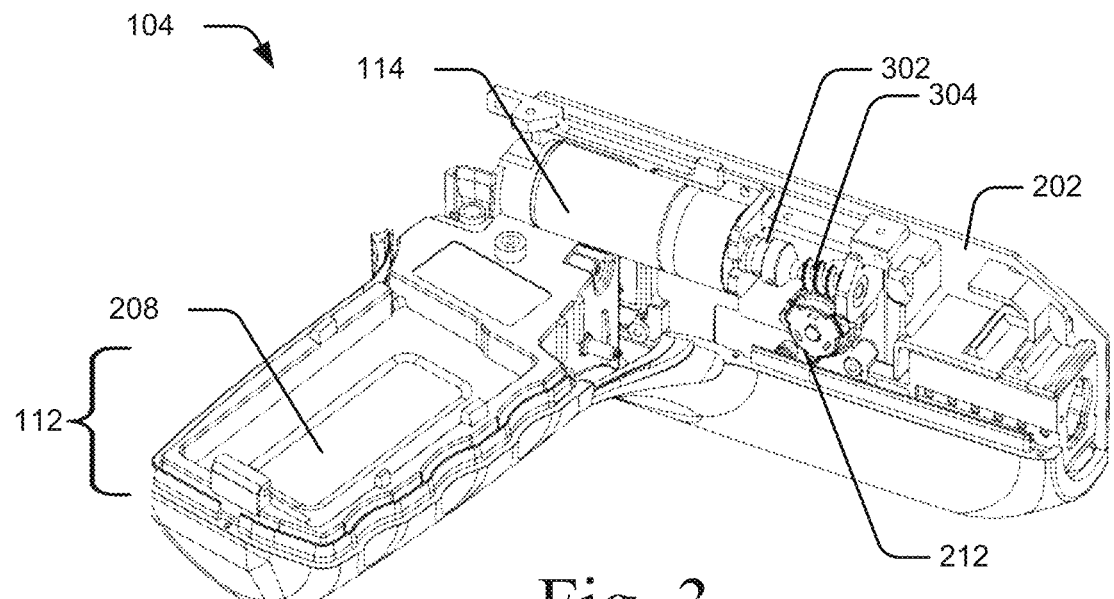
FIG. 3 illustrates sectional perspective view of the driver unit, according to an embodiment of the present subject matter.

FIG. 3 illustrate perspective view the driver unit 104, according to an embodiment of the present subject matter. The driver unit 104 of the biopsy device 100 includes the pressure subsystem 112, the prime-mover 114, and the control subsystem (not shown in the figure).

The prime-mover 114 is provided with the drive shaft 302, which is coupled with a worm 304. The worm 304 engages with a driver gear (not shown in figure) for operating the driving mechanism. The prime-mover 114 is housed in the mounting element 202, which is attached on top portion of the driver unit 104. The prime-mover 114 may be driven by a power source (not shown in figures) and may be one of direct current motor (DC), solar powered motor, or any other rotational mechanism.

In one embodiment, a magnet (not shown in figure) may be placed on the worm 304 and a corresponding PCB with sensor to read the same may be present in the driver unit 104. After a procedural cycle, the position of the coupler is different from the initial position. The magnet can ensure that a coupler (not shown in figure) present on the driver unit 104 is reset to the initial position after the probe unit has been removed. The resetting of the coupler enables attaching of a new probe unit on the driver unit 104.

The pressure storage chamber 208 may be housed below the prime-mover 114 and the pressure pump (not shown in figure) may be located beside the prime-mover 114. As shown, the pressure storage chamber 208 may be housed in a handle of the biopsy device 100.

The handle of the biopsy device 100 may also include a trigger button (not shown in figure), which may send signals to the control subsystem 116 on actuation. The control subsystem 116 may include one or more of microcontrollers, microprocessors, microcomputers, central processing units, and the like. In one embodiment, the control subsystem 116 may be installed in the handle of the biopsy device 100. The control subsystem 116 may receive signals from the pressure sensor 216 for determining the level of pressure in the pressure storage chamber 208. Subsequently, during the operation the control subsystem 116 may control valves to apply appropriate pressure in the lumen of the needle.

The pressure pump 204 generates a pressure which is stored within the pressure storage chamber 208 prior to procedure. In one embodiment, on actuating the trigger button, the solenoid valve is actuated to connect the pressure storage chamber 208 to the needle. The solenoid valve 212 may be installed within the mounting element 202 for controlling the pressure applied in needle.

Figure 4:
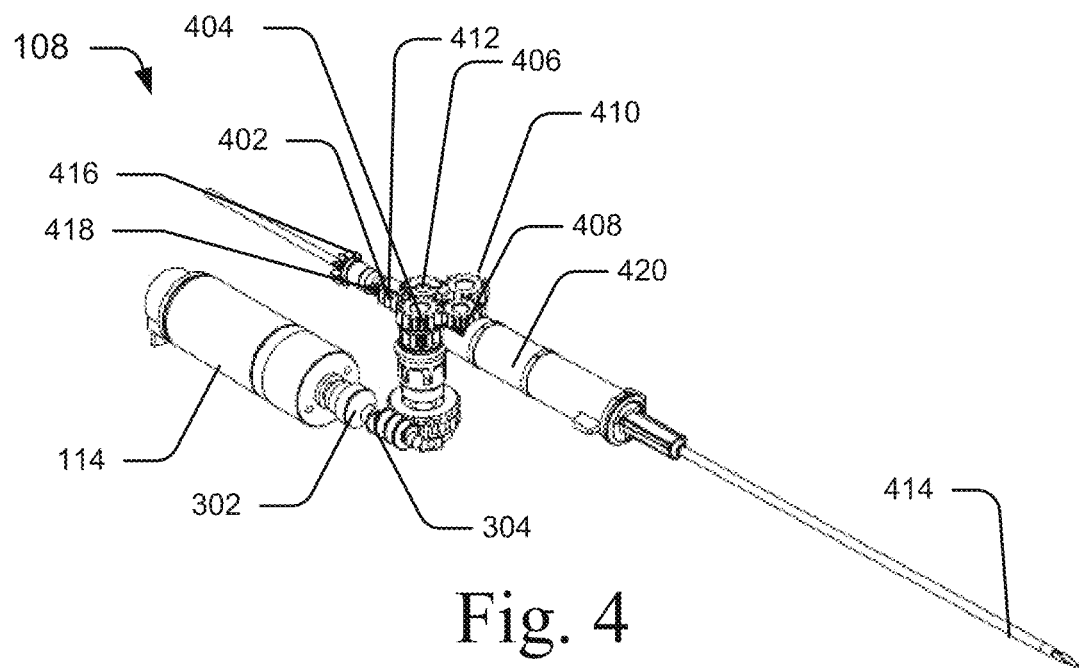
FIG. 4 illustrates perspective view of the driving mechanism, according to an embodiment of the present subject matter.

FIG. 4 illustrates a perspective view of the driving mechanism 108, according to an embodiment of the present subject matter. The driving mechanism 108 includes a gear rack 402, driver gear 404, a transmission gear 406, a stability gear 408, and at least one driven gear 410. The driver gear 404 is connected to the drive shaft 302 of the prime-mover 114, the gear rack 402, the transmission gear 406, and the stability gear 408. In one embodiment, the driver gear 404 has an elongated gear profile to engage with the driver gear 404 and the gear rack 402, which may be positioned on the shaft member 412. The gear rack 402 may include a plurality of teeth to engage with the driver gear 404 and the at least one driven gear 410 at respective intervals.

The rotational motion of the drive shaft 302 drives the driver gear 404, which in turn drives the transmission gear 406, the stability gear 408, and the at least one driven gear 410. The driver gear 404 is engaged with the gear rack 402 and drives the gear rack 402 to advance the shaft member 412 in the linear direction. In one embodiment, the shaft member 412 is hollow and the needle 414 is fixedly attached in the hollow passage. In one embodiment, the needle 414 may be formed as a hollow tube and the distal end of the needle 414 may include a converging section. The converging section may arcuately converge from wall of the hollow tube to form a piercing tip. Further, the converging section may also include an opening on lateral wall to form cutting edges to extract the tissue sample.

Further, the linear motion of the shaft member 412 projects the distal end of the needle 414 outside the cannula and pierces the organ of interest. The operation of the driving mechanism 108 and the projection of the needle 414 outside cannula may be performed when the cannula is inserted into the subject.

Further, a transitional gear 416 located at a proximal end of the shaft member 412 engages with the transmission gear 406 and produces a rotational motion of the shaft member 412. The shaft member 412 also includes a notch section 418, which engages or disengages the driver gear 404 and the at least one driven gear 410 at respective intervals. The notch section 418 may be a rounded cut-out that extends from the gear rack 402 ending just before the transitional gear 406 of the shaft member 412. The notch section 418 may temporarily halt the linear movement of the shaft member 412 by disengaging the gear rack 402 with the driver gear 404.

The rotational motion of the shaft member 412 rotates the needle 414 to extract a part of the tissue, which prolapses into the lumen of the needle 414. For instance, the rotational motion of the needle causes a transverse cut of tissue with cutting edges, without causing fragmentation of adjacent tissues.

Further, when the shaft member 412 completes rotation by a predetermined angle, for example 180°, the gear rack 402 engages with the at least one driven gear 410. Thus, the rotational motion of the shaft member 412, is converted back into linear motion, thereby causing the shaft member 412 to retract to its original position, and the needle to travel back through the cannula and retract to its original position.

In another embodiment, the distal end of the shaft member 412 is provided with container 420 for storing fluid, such as a haemostatic agent or any other medicament. The fluid may be provided through the cannula to the site where the needle extracts the tissue. In another embodiment, the container 420 is provided with an adapter such that, the adapter aids in holding the cannula.

As shown, the axis of the at least one driven gear 410 is in-line with the axis of the driver gear 404 and the axis of the transmission gear 406 is in-line with that of the stability gear 408. The stability gear 408 provides strength and stability to the functioning of the driver gear 404, the transmission gear 406, and the at least one driven gear 410.

In one embodiment, the driver gear 404, the transmission gear 406, the stability gear 408, and the at least one driven gear 410 are of same size. In one embodiment, the gearing ratios of the driver gear 404 and the at least one driven gear 410 are configured with equivalent gear ratios. In another embodiment, the gearing ratios of the transmission gear 406 with the driver gear 404 are configured to have higher gear ratios. Further, in another embodiment, the gearing ratios of the transmission gear 406 with the at least one driven gear 410 are configured to have lower gear ratios.

Further, the shaft member 412 may be located between the driver gear 404 and the at least one driven gear 410. The shaft member 412 at its proximal end is provided with a transitional gear 416. The transitional gear 416 is provided with intermittent gear teeth to selectively engage with the transmission gear 406 when the shaft member 412 moves linearly for a predetermined length such that the transitional gear 416 engages with the transmission gear 406. The shaft member 412 travels linearly and the needle 414 fitted within the shaft member 412 is actuated towards the tissue of interest inside the subject.

Figure 5:
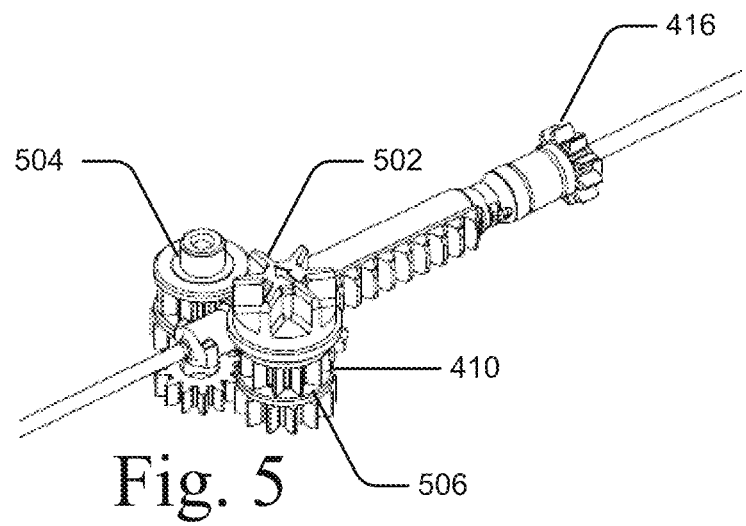
FIG. 5 illustrates top view of the driving mechanism, according to an embodiment of the present subject matter.

FIG. 5 illustrate a perspective bottom view of the driving mechanism, according to an embodiment of the present subject matter. In one embodiment, the bottom of the driver gear 404 is provided with a driver gear coupler 502 for coupling the driver gear 404 with a bottom cover (not shown in figure) of the probe unit 102. Similarly, the bottom of the at least one driven gear 410 is provided an at least one driven gear coupler 504 to couple with the bottom cover of the probe unit 102.

Further, the probe unit 102 may be provided with protrusions to facilitate mounting of the gears of the driving mechanism 108. For example, the top portion of the gears may couple with the protrusions by one of a male-female coupling, a snap fit coupling, thread coupling, or the like. In one embodiment, the driver gear 404, a transmission gear 406, the stability gear 408, and at least one driven gear 410 are mounted on each of the protrusions provided on the probe unit 102. In another embodiment, the at least one driven gear 410 and the driver gear 404 may be provided with roller supports 506 to reduce the friction losses in the gear profile. Further, as shown, the transitional gear 416 may include intermittent gear teeth to engage with the transmission gear 406 at the end of the linear advancement of the shaft member 412.

Figure 6:
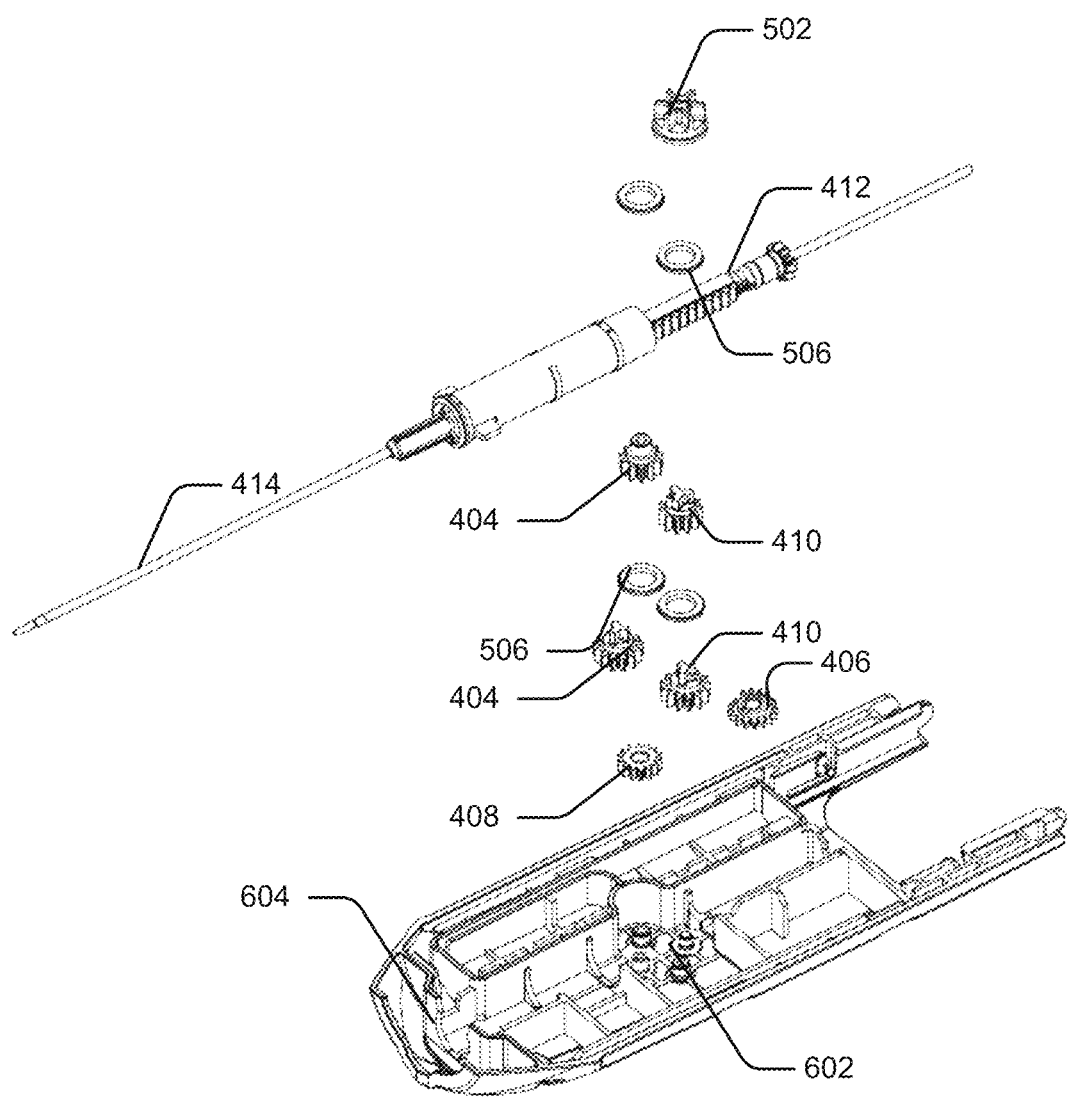
FIG. 6 illustrates exploded view of the driving mechanism in probe unit, according to an embodiment of the present subject matter.

FIG. 6 illustrates exploded view of the driving mechanism 108 in the probe unit 102 from bottom, according to an embodiment of the present subject matter. The probe unit 102 may include protrusions 602 for accommodating one or more of the driver gear 404, the transmission gear 406, the stability gear 408, and the at least one driven gear 410. As shown in FIG. 6, the driver gear 404 and the at least one driven gear 410 are installed over roller supports 506 to prevent friction losses arising out of rotation of the driver gear 404 and the at least one driven gear 410, which are configured with elongated gear profiles.

Further, the probe unit 102 may include cut-outs 604 to facilitate the linear and rotational motion of the needle 414 and the shaft member 412. In one embodiment, the shaft member 412 can be rotated from about 0° to about 180°. In another embodiment, the shaft member 412 can be rotated by a predetermined angle. In another embodiment, the driving mechanism 108 is configured on the probe unit 102, which can be detached after use. Further, the tissue sample container 110 and injection unit comprising the needle 414 may also be detached for disposal, examination, storage, or transportation of the tissue sample.

Figure 7A:
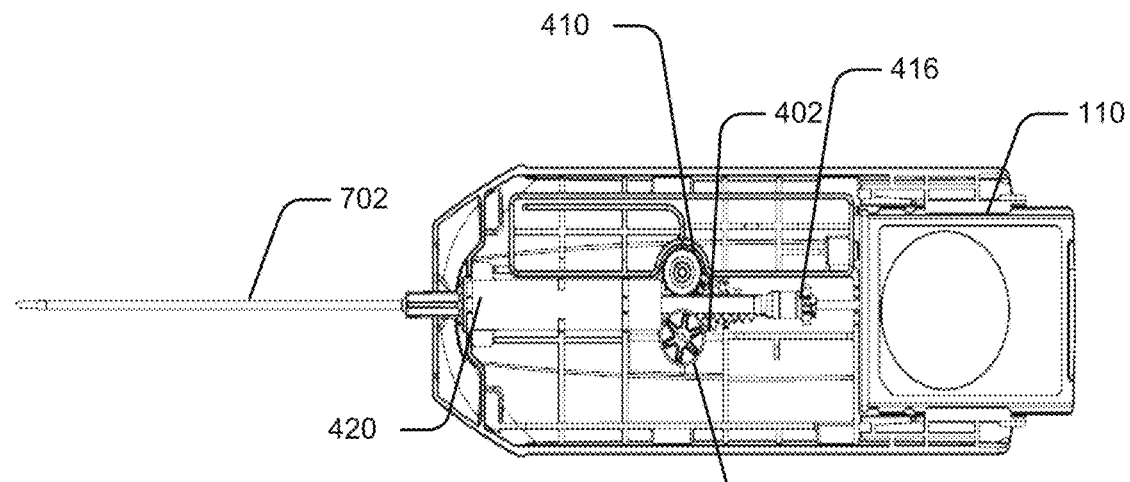
FIG. 7A illustrates shaft member at initial position, according to an embodiment of the present subject matter.

FIG. 7A illustrates a bottom-view of the driving mechanism 108 at its initial position according to an embodiment of the present subject matter. The gear rack 402 configured on the shaft member 412 is in contact with the driver gear 404 at an initial position.

The driver gear 404 is connected to the drive shaft 204 of the prime-mover 114, the gear rack 402, the transmission gear 406, and the stability gear 408. The driver gear 404 may have an elongated gear profile to engage with the drive shaft 304 and the gear rack 402. The rotational motion of the drive shaft 302 rotates the driver gear 404, which in turn drives the driver gear to initiate linear motion of the gear rack 402.

The gear rack 402 engages with the driver gear 404 and the shaft member 412 moves linearly. The linear motion of the shaft member 412 projects the needle 414 outside the cannula 702. The needle 414 is projected outside cannula 702 when the injection unit 106 is inserted into the subject.

In one embodiment, the container 420 provided at distal end of the shaft member 412 is equipped with a piston-like arrangement (not shown in figure). In another embodiment, the distal end of the shaft member 412 is capable of plunging the piston-like arrangement linearly, in order to infuse the fluid present in the container 420 into the subject. For instance, the fluid may be provided through the cannula to the site where the tissue is extracted. Further, the amount of the medicament infused can be controlled during the linear movement of shaft.

Further, after the gear rack 402 disengages with the driver gear 404, the transitional gear 416, which is located at the proximal end of the shaft member, engages with the transmission gear 406.

Figure 7B:
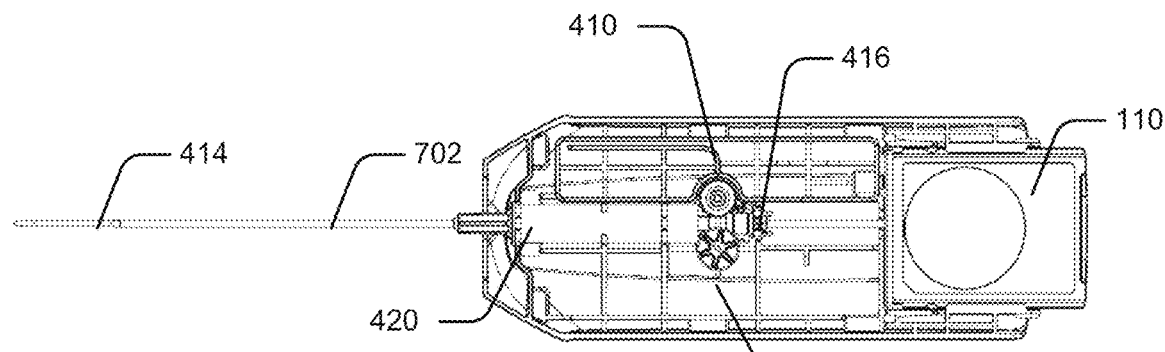
FIG. 7B illustrates shaft member at displaced and transition position, according to an embodiment of the present subject matter.

FIG. 7B illustrates a bottom-view of driving mechanism 108 at displaced position, according to an embodiment of the present subject matter. At the displaced position, the gear rack 402 of the shaft member 412 disengages from the driver gear 404. The notch section 418 on the shaft member 412 disengages the driver gear 404 from the gear rack 402 of the shaft member 412. The transitional gear 416 provided at proximal end of the shaft member 412 engages with the transmission gear 406 at the displaced position (DP).

Further, the transitional gear 416 upon engagement with the transmission gear 406 revolves the shaft member 412 about its axis. The transitional gear 416 may have intermittent gear teeth to aid in the rotation of the shaft member 412 at specific angles. The revolution of the shaft member about the shaft axis takes place such that the gear rack of the shaft member engages with the at least one driven gear 410. The shaft member 412 during this transition, rotates the needle 414 within the subject such that, the distal end of the needle 414 shears off part of tissue from the subject.

Figure 7C:
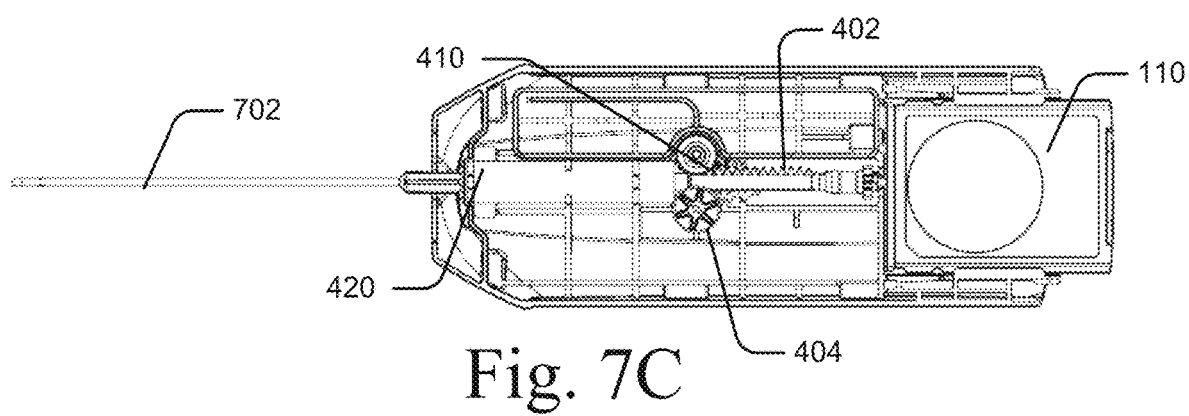
FIG. 7C illustrates shaft member at final position, according to an embodiment of the present subject matter.

FIG. 7C illustrates a bottom-view of driving mechanism 108 at final position (FP) according to an embodiment of the present subject matter. The at least one driven gear 410 engages with the gear rack 402 of the shaft member 412 and linearly actuates the shaft member 412 in a direction opposite to that shown in FIGS. 7A and 7B. The needle 414, which is previously projected in the subject, is retracted when the shaft member 412 actuates linearly from transitional position (TP) to the final position (FP). The gear rack of the shaft member 412 is disengaged from the at least one driven gear 410 when the shaft member 412 reaches final position (FP).

In one embodiment, the distal end of the shaft member 412 disengages from the piston-like arrangement during the retraction of the shaft member 412. In one embodiment, disengagement of the shaft member 412 from the at least one driven gear derails the driving mechanism 108 and restricts consecutive use of the driving mechanism 108.

FIG. 8 illustrates a sectional side view of the probe unit 102 according to an embodiment of the present subject matter. In one embodiment, the needle 414 is fixed to the shaft member 412 as described earlier, the distal end of the needle 414 at the time of operation pierces through the subject for extraction of tissue sample. The proximal end of the needle 414 is located within the tissue sample container 110 such that, the tissue retrieved from the subject is contained for further processing. The needle 414 comprising the lumen is connected to the pressure subsystem 112 for extraction of tissue sample.

In one embodiment, during biopsy, negative pressure from the pressure storage chamber 208 is provided within the lumen of the needle 414 at the time of incision into the subject for drawing the tissue sample into the lumen of the needle 414. The negative pressure is later reapplied for collecting it from the needle 414 lumen into the tissue sample container 110.

In another embodiment, positive pressure is supplied by the pressure pump 204 to transfer the tissue sample extracted within the lumen of the needle 414 into a separate external tissue sample container.

FIG. 9 illustrates bottom view of the probe unit with auxiliary container according to an embodiment of the present subject matter. An auxiliary container 902 may be used for storing fluid, which may be configured with an auxiliary piston-like arrangement (not shown in figure). The auxiliary piston-like arrangement is used to infuse the fluid stored within the auxiliary container 902 into the subject.

In one embodiment, the auxiliary container 902 may be connected to the adapter through a channel such that, the fluids from the container 420 and the auxiliary container 902 may be mixed within spiral grooves (not shown) before delivery into the subject. The medicaments or haemostatic agent may travel from the container 420 within the cannula and into the subject through the cannula, which is concentrically covering the needle 414.

Further, an auxiliary driven gear (not shown in figure) may be engaged to the driver gear 404 such that, the driver gear 404 drives the auxiliary driven gear. The auxiliary driven gear engages with the auxiliary shaft member (not shown in figure) having an auxiliary gear rack. The auxiliary shaft member is provided with an auxiliary notch section so as to disengage the auxiliary driven gear from the auxiliary gear rack.

The auxiliary shaft member may actuate linearly from initial position (IP') to final position (FP'). Once the auxiliary shaft member reaches the final position (FP'), the auxiliary driven gear is disengaged from the auxiliary gear rack provided on the auxiliary shaft member. Thus, the distal end of the auxiliary shaft member drives the auxiliary piston-like arrangement provided within the auxiliary container.

In one embodiment, the auxiliary container 902 may have a minimum volume 'x' times the amount of fluid to be delivered during each biopsy cycle, 'x' being the number of biopsy cycles. The fluid may be required for multiple cycles and may be prepared and loaded before the probe is inserted into the patient's body. The fluid may be filled in the auxiliary container 902 and the container 420 through a cap 206 provided on the probe unit 102. The fluid present in the container 420 is delivered to the biopsy site during the forward motion of the needle. During retraction of the needle, the suction generated in the container 420 draws the fluid from the auxiliary container 902 into the container 420, thus readying it for the next biopsy cycle.

In one embodiment, the auxiliary container 902 and the container 420 may be connected by a one-way valve (not shown in figure). The one-way valve may prevent the medicament or fluid present in the container 420 back to the auxiliary container 902.

Further, the biopsy device 100 with the auxiliary container 902 may be used when multiple tissue samples are required to be extracted, collected, and infused with fluids. For instance, in the biopsy of kidneys, it may be required to extract and collect two or more samples of tissues. In one embodiment, the auxiliary container 902 may be directly connected to the needle 414 through a conduit for transferring fluid.

The above embodiments with reference to the FIG. 9 may be used in cases where the minimum number of samples required are 2-3 samples, such as in kidney biopsy. Therefore, the device may be used repetitively to execute multiple sequences of tissue extraction and collection. The same probe unit can be used for a single patient to collect multiple samples in a single operation of the device by just replacing the tissue sample container 110. Therefore, the fluid may be provided using the auxiliary container each time the extraction is performed.

In another embodiment, the biopsy device 100 may not include the container 420 and the auxiliary container 902. For instance, in case of biopsy procedures for certain less vascular organs, such as prostate and breast, it is not an essential requirement to deliver fluids such as haemostatic agents. Therefore, the probe unit may not include the container 420 and the auxiliary container 902.

Figure 10A:
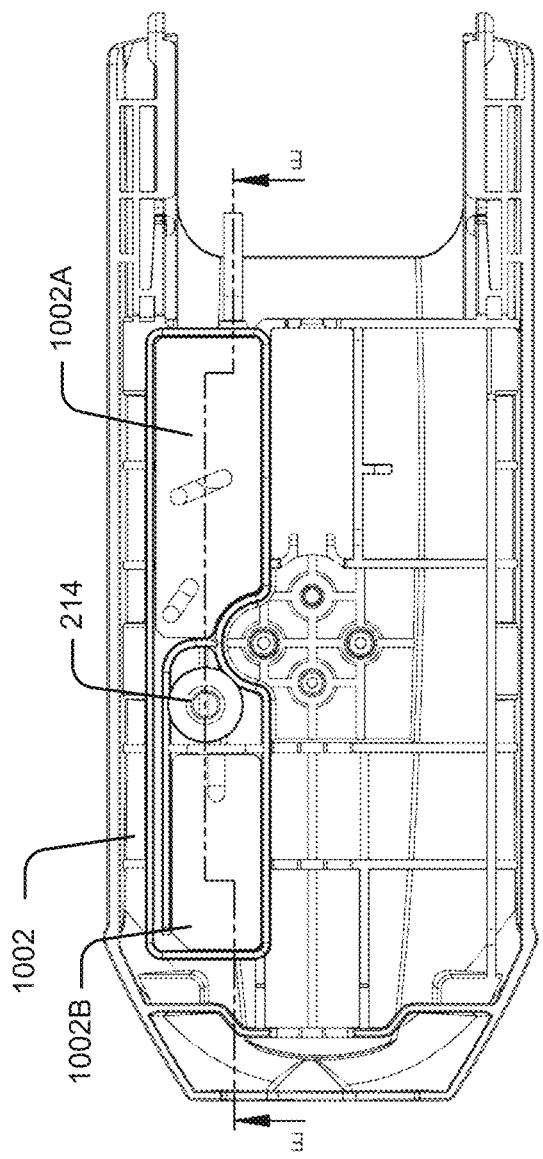
FIGS. 10A and 10B illustrates a bottom and sectional view of the filter chamber, according to an embodiment of the present subject matter.
Figure 10B:
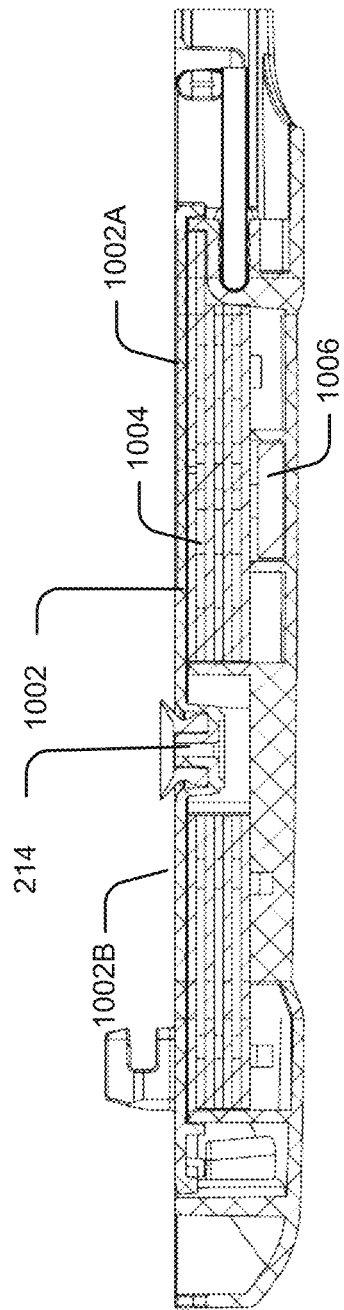

FIGS. 10A and 10B illustrate a top view and sectional view of filter chamber 1002 according to an embodiment of the present subject matter. In an embodiment, the filter chamber 1002 is part of the filtering mechanism 111 (as shown in FIG. 1). The filter chamber 1002 at one end is connected to a conduit (not shown in figure) that connects to a second compartment (not shown in figure) of the tissue sample container 110. The other end of the filter chamber 1002 is connected to the interfacing element 214. The interfacing element 214, which serves as an interface between the driver unit 104 and the probe unit 102 and provide negative pressure or positive pressure from the pressure storage chamber 208 to the filter chamber 1002. The filter chamber 1002 is coupled to and provided in the tissue sample container 110.

In one embodiment, the filter chamber 1002 includes primary chamber 1002A and secondary chamber 1002B. The two chambers include a series of filter members 1004 stacked one above the other. The filter chamber 1002 may be connected to the interfacing element 214 via conduits to enable application of pressure. For instance, the control subsystem 116 may control the solenoid valve to apply a negative pressure through the interfacing element 214 and to the filter chamber 1002.

Due to the application of the negative pressure, the impurities of the tissue sample contained in the tissue sample container 110 are absorbed into the filter chamber (primary) due to the negative pressure from the pressure storage chamber 208 during tissue prolapse. The impurities may be blotted by the plurality of filter members 1004 such that, the impurities are contained within the filter chamber 1002. In addition, the filter chamber includes empty spaces to drain residual fluid impurities. In one embodiment, a hydrogel pad 1006 may be placed in at least one of the empty spaces to absorb the fluid impurities. The hydrogel pads 1006 may be used in cases where the probe unit 102 is used for multiple sampling.

The secondary stage may be an additional chamber for increased efficiency in capture of impurities. The tissue sample after filtration process is relieved of impurities and the sample can be used for further analysis.

In one embodiment, the impurities contained within the filter chamber 1002 after biopsy can be discarded by detaching the probe unit 102 and disposing the same to prevent spread of infectious diseases. Additionally, the disinfectant may be disposed on the conduits to prevent pathogens to travel towards the driver unit 104.

In another embodiment, the plurality of filter members 1004 may be disposed with a layer of disinfectants for deactivating harmful pathogens or viruses to reduce biohazard and/or infection during and post procedure handling of the biopsy device 100.

Figure 11:
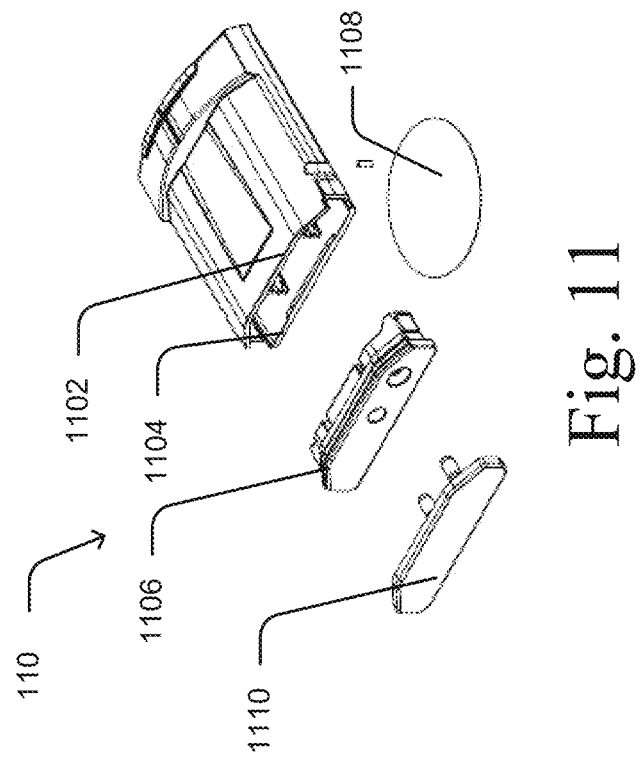
FIG. 11 illustrates exploded view of the tissue sample container, according to an embodiment of the present subject matter.

FIG. 11 illustrates an exploded and perspective view of the tissue sample container 110, according to an embodiment of the present subject matter. The tissue sample container 110 is detachably coupled to a proximal end of the probe unit 102. In one embodiment, the tissue sample container 110 may be compartmentalized into two functional compartments—a first compartment 1102 and the second compartment 1104.

The first compartment 1102 receives the tissue sample from the subject through the lumen of the needle 414. The tissue sample container 110 contains a plate with serrations at one end that separates the first compartment 1102 and the second compartment 1104. The serrations allow fluids to seep into the second compartment 1104 thus separating the fluid from the sample. The second compartment 1104 includes a conduit to connect to the filter chamber. In one embodiment, the conduit provided within the second compartment of the tissue sample chamber 108 is hollow and allows pressure to pass through from the pressure storage chamber 208 via the filter chamber.

In one embodiment, the tissue sample container 110 is provided with a front cover 1106, which has an inlet opening wherein the needle 414 is capable of protruding into the tissue sample chamber 108. Another inlet opening is provided for the conduit to form a pressure path. A groove is provided on the front cover of the tissue sample container 110 for removing the front cover 1108 to retrieve the tissue sample. In one embodiment, the inlet opening is capable to receive the proximal end of the needle 414.

In one embodiment, tissue fixing agents are capable of being injected into the tissue sample container 110 to preserve the tissue sample from deterioration during transport of the tissue sample to the pathology lab. Additionally, the tissue fixing agents aid in preservation and sterile handling of the tissue sample within the tissue sample container 110.

Further, a Near Field Communication (NFC) tag 1108 may be provided on the tissue sample container 110. The NFC tag 1108 is coded with a unique identification number to prevent potential tampering or sabotage of the tissue sample container 110. The tissue sample container 110 can be enclosed using a lid 1110 when it is removed from the probe unit. The lid 1110 may isolate the tissue sample from the environment and prevent spillage.

In one embodiment, the unique identification number is at least one of batch number, serial manufacturing number, coded number or any other identification which serves the purpose.

In one embodiment, the NFC tag 1108 can be used to wirelessly transfer data to a data collection device. In another embodiment, the NFC tag 1108 wirelessly transmits data to a tracking device for locating the device. The NFC tag 1108 may prevent reuse of the tissue sample container 110 as the coded NFC tag 1108 allows only for a single operation at any given time. In other embodiments, other ways of tagging the sample container as well as tracking the device, including, but not restricted to RFID and GPS, may be used, as known in the art.

In one embodiment, the tissue sample container 110 is provided with a magnet sensed by the sensor in the driver unit. If there is no detection by the sensor, it indicates the tissue sample container is either absent or placed incorrectly. Thus, it ensures that the tissue sample container 110 is in its position before taking a biopsy.

Figure 12:
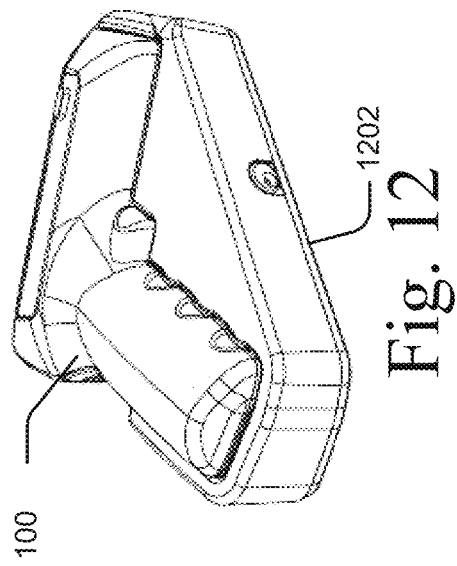
FIG. 12 illustrates a docking unit coupled to the device, according to an embodiment of the present subject matter.

FIG. 12 illustrates a docking unit for docking the biopsy device 100, according to an embodiment of the present subject matter. The docking unit 1202 may be a peripheral device connected to the biopsy device 100 for charging battery of the biopsy device 100.

The docking unit 1202 and the biopsy device 100 may be connected with a device mating connector (not shown in figure) that provides for active electrical connection. Further, the docking unit 1202 may include a battery charging circuit for charging the battery of the biopsy device 100.

Figure 13:
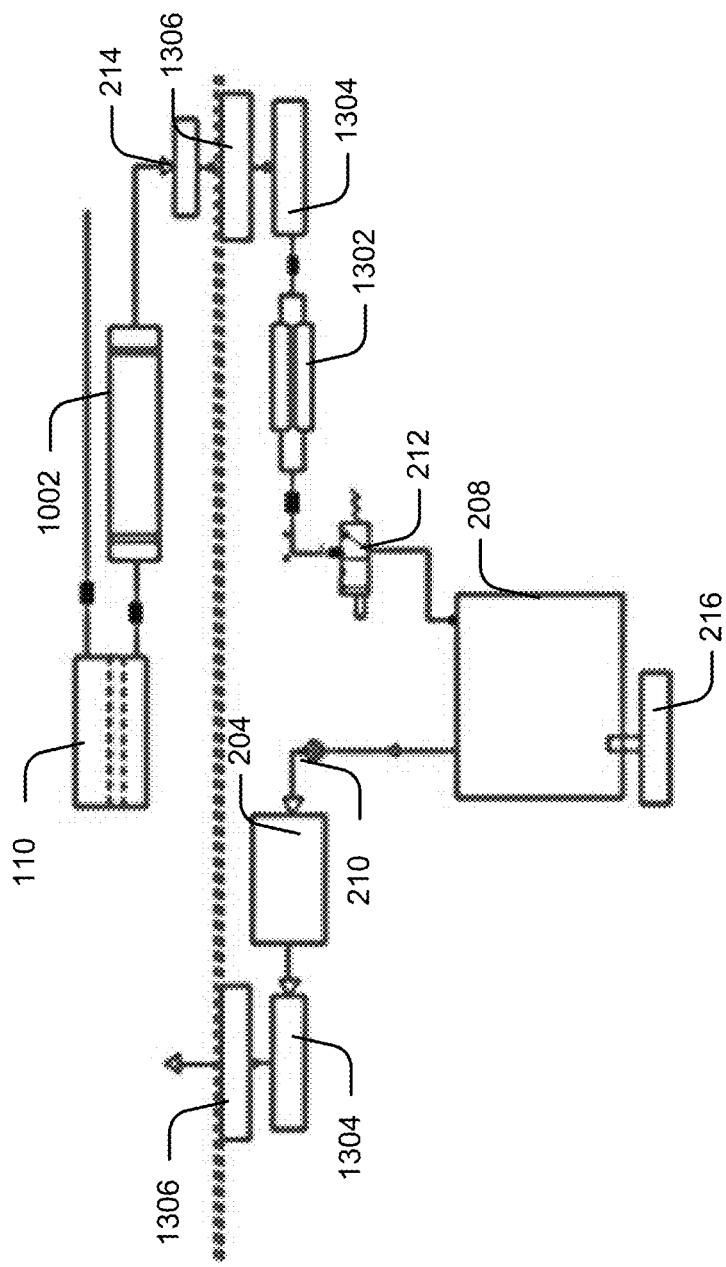
FIG. 13 illustrates pressure flow path within the device, according to an embodiment of the present subject matter.

FIG. 13 illustrates negative pressure flow path of the pressure subsystem 112 within the biopsy device 100, according to an embodiment of the present subject matter. The pressure subsystem 112 include the pressure pump 204 having inlet port and outlet port. In one embodiment, the pressure pump 204 when actuated generates negative pressure, which is stored within the pressure storage chamber 208.

During operation of the biopsy device 100, the pressure pump 204 generates negative pressure or positive pressure based on the requirement of the tissue extraction procedure implemented in the biopsy device 100. In one embodiment, the pressure pump 204 generates negative pressure and stores it within the pressure storage chamber 208 for immediate procedural use.

In one embodiment, the pressure stored in the pressure storage chamber 208 readily supplies the negative pressure or positive pressure according to the values defined by the tissue extraction procedure implemented in the device at various stages of biopsy. The pressure storage chamber 208 is equipped with a pressure sensor 216 for indicating the amount of pressure available for use to the user. For instance, the amount of pressure available may be displayed in a display unit, which is positioned on the driver unit 104 of the biopsy device 100.

In one embodiment, the pressure pump 204 draws in air from the pressure storage chamber 208 and generates negative pressure. A check valve 210 is installed in-between and coupled between the pressure storage chamber 208 and the pressure pump 204 so as to regulate the flow of negative pressure from the pressure pump 204.

The solenoid valve 212 is coupled to the pressure storage chamber 208 such that, the solenoid valve 212 controls the pressure provided by the pressure storage chamber 208 to the probe unit 102. The solenoid valve 212 allows stored pressure into the interfacing element, which generates pressure based on the requirement of the user.

In one embodiment, at least one inline filter 1302 is connected in parallel between the interfacing element 214 and the solenoid valve 212 via a T-joint. This ensures that the air flow from the needle 414 to the pressure pump 204 via the interfacing element 214, solenoid valve 212, and the pressure storage chamber 208 is cleared of impurities even if one of the filters is clogged with repeated use of the device. A hydrophobic filter 1304 is also present between the interfacing element 214 and the inline filters to keep the path free of any fluids.

In one embodiment, the pressure generated at the interfacing element 214 travels through the filter chamber for filtering the impurities from the tissue sample stored at the tissue sample container 110.

The pressure pump 204 empties the air present within the pressure storage chamber 208 to the atmosphere via the outlet port while generating negative pressure. The hydrophobic filter 1304 present at the outlet port ensures that no liquid seeps into the pump 204. A wire mesh 1306 may also be present to protect it from external particulate matter.

In one embodiment, the device provides alert to the user on the status of the biopsy device during biopsy procedure. The alert may be provided by one of a buzzer, LED, or the display unit.

Figure 14:
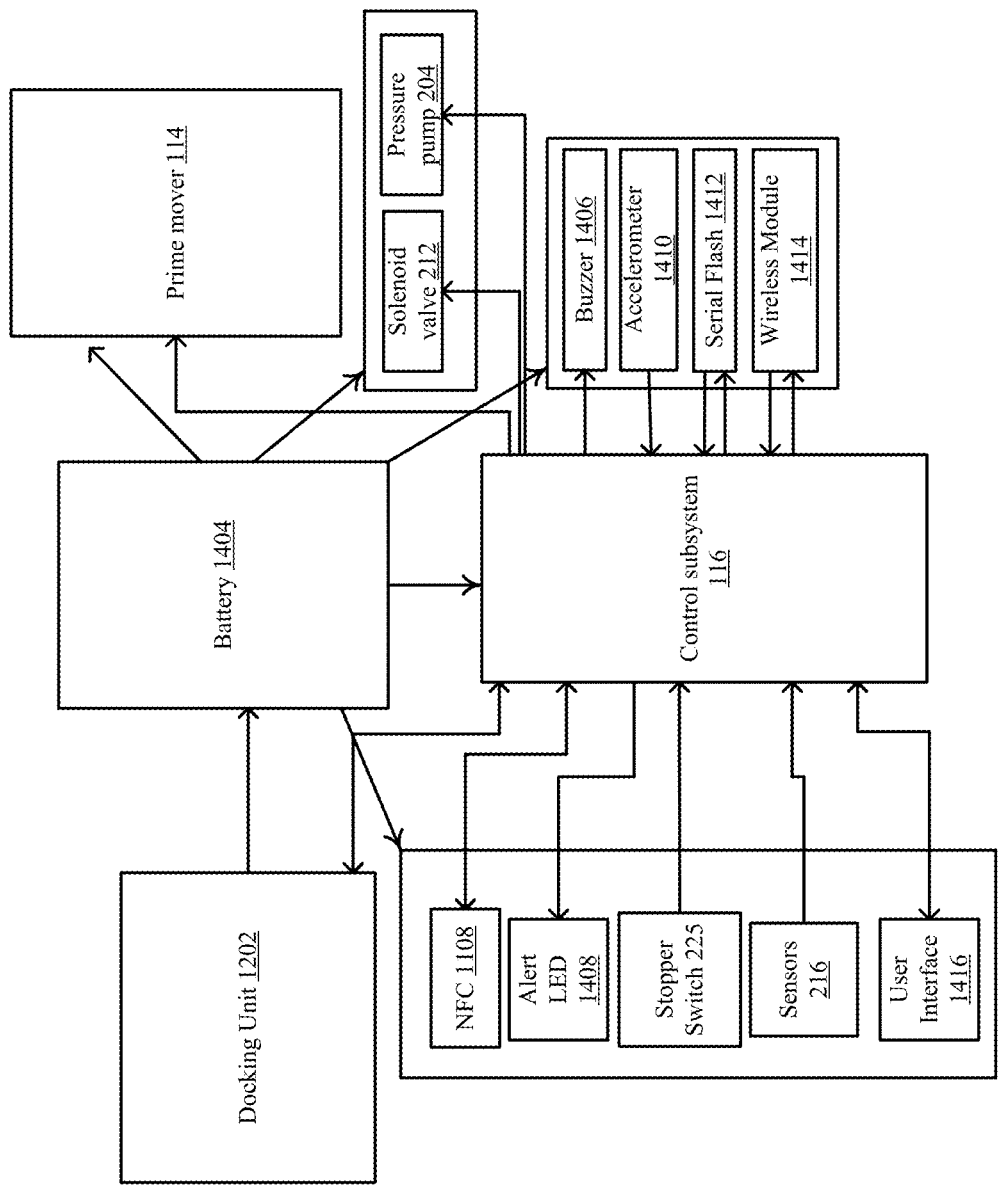
FIG. 14 illustrates a block diagram of the control subsystem, according to an embodiment of the present subject matter.

FIG. 14 illustrates a block diagram of the control subsystem 116 according to an embodiment of the present subject matter. The control subsystem 116 may be implemented as one or more microcontrollers, microprocessors, microcomputers, digital signal processors, central processing units, logic circuitries, and/or any devices that manipulate signals based on operational instructions.

In one embodiment, the control subsystem 116 may be implemented as a microcontroller for controlling the various components of the device and responsible for system sleep and wake-up. For instance, the microcontroller controls and/or communicates with a docking unit 1202, prime-mover 114, NFC 1108, pressure pump 204, and other components. In one embodiment, the control subsystem 116 may include a timer, for example, a watch dog timer, to reset the microcontroller in case of any error, for example, suspension of activity of the biopsy device 100.

The sensors provided in the biopsy device 100 may provide information regarding the status of various components to the control subsystem 116. For example, the pressure sensor 216 may detect the pressure in the pressure storage chamber 208 and send signals to the control subsystem 116. The control subsystem 116 is to receive signals from a plurality of pressure sensors in the pressure system. The control subsystem 116 may issue commands to the pressure pump 204 to generate a partial vacuum in the pressure storage chamber 208 based on the signal and organ specific requirement as different organs may require different amount of pressure. The control subsystem 116 may, based on the signals received from the plurality of pressure sensors, control the solenoid valve 212 and the check valve 210. In an embodiment, the control subsystem 116 may control the solenoid valve 212 to control pressure provided to the probe unit 102 and the check valve 210 to prevent reverse flow of pressure. In an embodiment, the control subsystem 116 also controls the prime-mover 114 to actuate the driving mechanism 108.

In one embodiment, the control subsystem 116 may receive the status of the probe unit 102, for example, by using the needle depth adjuster 218. For example, it may receive inputs from sensors for sensing the needle depth adjuster 218 position and probe unit lock. The control subsystem 116 may be provided inputs regarding whether the needle depth adjuster device 218 has been pressed against the subject from the stopper switch 225 and indicate the same to the user. The control subsystem 116 may also receive input from NFC tracking device and Hall sensors for detecting the presence of tissue sample container 110 in probe unit 102. The control subsystem may receive inputs from sensors to determine if driver unit has been placed on the docking unit. The control subsystem 116 may receive inputs from the Hall sensors relating to position of buttons, for examples, right and left buttons provided on the driver unit used for ejection of the probe unit 102. Based on Hall sensor signals, the control subsystem 116 may compute length of the needle.

Further, a docking unit 1202 may be connected to the biopsy device 100 for charging battery 1404. The docking unit and the biopsy device 100 may be connected with a device mating connector that provides for active connection between prime-mover 114 and docking unit 1202.

The control subsystem 116 may be coupled to a buzzer 1406 for providing an alert signal for, among other things, to indicate an error in the biopsy operation.

The control subsystem 116 may also be coupled to an Alert LED 1408 for providing a visual alert indication to the user. The Alert LED 1408 may be provided on the driver unit 104 of the biopsy device 100. The LEDs may indicate the sequence of operation, for example, if orange light is emitted then it may indicate that the biopsy procedure is in progress and white light may indicate that the sample has been collected in the tissue sample container. In case of alerts condition, for example, a tissue sample container has been ejected, an orange light may be used etc. It is to be understood that colours as indicated herein are examples only and are not to be construed as limiting.

In one embodiment, an accelerometer 1410 in the device may be used for determining the physical orientation of the device. In one embodiment, the accelerometer 1410 may be used for detecting the vertical alignment of the biopsy device 100 when sample travels to the tissue sample container 110. Further, the accelerometer 1410 can detect dormant condition of the biopsy device 100 based on which the control subsystem 116 may put the device in sleep mode, thus, conserving battery power.

The control subsystem 116 receives event log data and accesses the device firmware, which may be stored in serial flash 1412. The control subsystem 116 may communicate with a wireless module 1414 or connection, such as Bluetooth, to receive log data from the driver unit 104 to any application, for example, on a remote device. In an embodiment, the wireless module 1414 is the wireless module 111 of FIG. 1. Further, the control subsystem 116 may be programmed remotely, for example, by Over the Air (OTA) programming.

Further, user interface 1416 through OLED display and navigation buttons is controlled through the OLED and selection switch. The LED present on the driver unit below the sample container illuminates on detection of the sample in the chamber. The user interface 1416, in an embodiment, also includes the trigger button as previously explained. Actuation of the trigger button along with the stopper switch 1402 status sends signals to the control subsystem 116 for switching on the biopsy device 100 and to begin an operational cycle. In an embodiment, the battery 1404 supplies power to all the components as discussed above.

Figure 15:
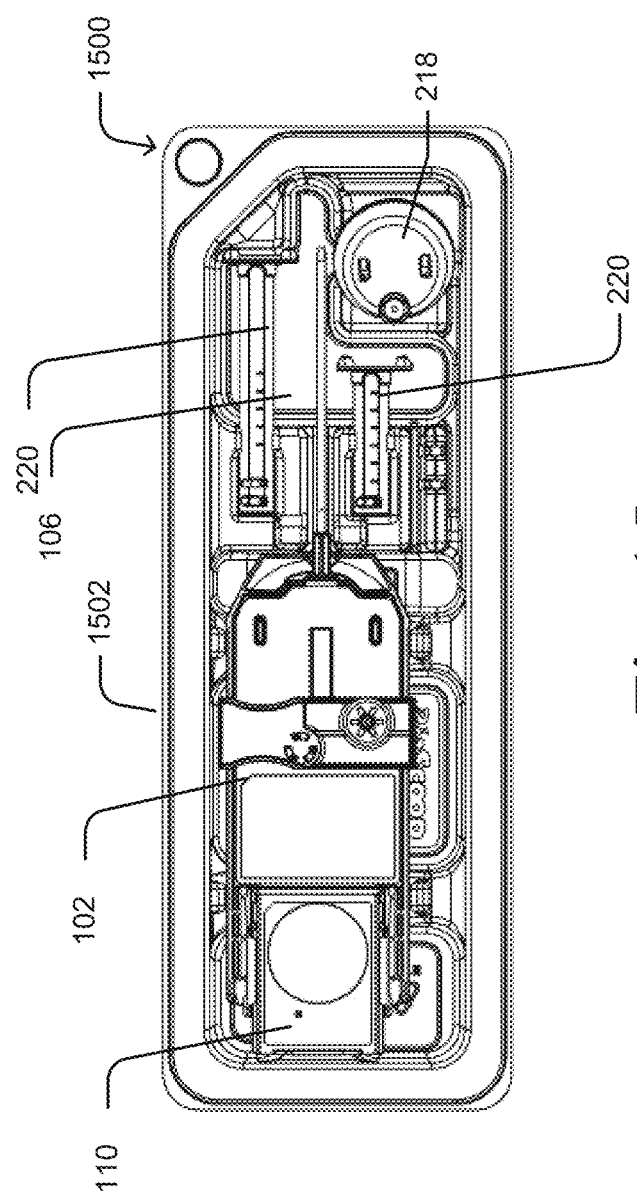
FIG. 15 illustrate a top view of the packaging tray for probe unit, according to an embodiment of the present subject matter.

FIG. 15 illustrates top view of a packaging tray 1500 for the probe unit 102, according to an embodiment of the present subject matter. The packaging tray 1500 may be an ergonomic packaging unit for enclosing various components of the probe unit 102. The packaging tray 1500 may include a cover 1502 and a plurality of cut-outs. As mentioned earlier, the same driver unit 104 may be used multiple times with different probe units 102 for performing different procedures. Accordingly, each probe unit 102 may be packed and sold separately.

In one embodiment, the cover 1502 may be heat sealed on the tray to keep the probe unit 102 in the tray sterile. Further, the components of the probe unit 102 may be safely placed in the plurality of cut-outs. As shown, the needle depth adjuster 218, the tissue sample container 110 (at least one), the probe unit 102 may be placed separately in the plurality of cut-outs of the packaging tray 1500. In one embodiment, a single cut-out may be provided for placing an assembled probe unit 102.

The cover 1502 may be peeled out before the biopsy procedure and the components of the probe unit 102 may be removed from the cut-out and then assembled. In one embodiment, the packaging tray 1500 may be made from plastic. In other embodiments, the packaging tray may be made from any other material.

Therefore, the above described device comprising a driving mechanism 108 and a pressure subsystem 112 used in the extraction and collection of tissue sample from a subject is disclosed. The device is a handheld portable diagnostic device, wherein a needle 414 is actuated by a driving mechanism which drives the needle 414 into the subject. The extraction of tissue sample is assisted by the pressure subsystem 112.

In one embodiment, a single prime-mover is used to linearly actuate the needle 414 into and out of the subject and rotate the needle 414 as opposed to using separate driving units for each of these three motions.

In one embodiment, the biopsy device consumes less power as compared to devices equipped with more than one prime-mover for achieving different types of motion.

In one embodiment, the biopsy device equipped with the single prime-mover aids in portability of the device.

In one embodiment, the combination of three different types of motion such as linear advancement, retraction and rotation is achieved using minimal number of gearing components and with single input motion rendering a compact design.

In one embodiment, the integrated mechanism consisting of the driving mechanism and the pressure subsystem 112 aids in piercing the subject while instantaneously supplying negative pressure to collect the tissue sample during forward travel, rotating the needle 414 within the subject for shearing part of the tissue while intermittently stopping the negative pressure, retracting the needle 414 out of the subject and supplying negative pressure to collect the tissue sample within the tissue sample container all in one sequence of biopsy procedure.

In one embodiment, the shaft member 412 disengages from the at least one driven gear as it reaches its final position, thereby rendering the driving mechanism unusable.

In one embodiment, the fluid from the container 420 and/or auxiliary container infuses into the subject and performs a secondary medical function such as stopping internal bleeding of the organs, thus avoiding medical complications.

In one embodiment, use of the biopsy device minimizes the clinical requirement of a high level of surgical skill and dexterity for performing the percutaneous biopsy procedure.

In one embodiment, the driving mechanism encased within the probe unit is disposed after single use, avoiding re-use of needle 414.

In one embodiment, the filter chamber provided in the probe unit isolates the infectious pathogens and prevents spreading of infectious diseases.

In one embodiment, the shaft member once disengaged from the at least one driven gear cannot be realigned to the driver unit for reuse without damaging the drive mechanism, thereby preventing the abuse of contaminated needle 414.

In one embodiment, the notch section resembles a clutch for disengaging the driver gear from the gear rack avoiding additional clutch mechanisms or prime-movers.

In one embodiment, the device is designed so as to accomplish forward linear movement of the needle 414 into the subject and retraction from the subject by a single prime-mover. Additionally, the retraction of the needle 414 into the cannula minimizes the probability of needle prick injuries while handling the device.

In one embodiment, the pressure pump 204 generates pressure and stores within the pressure storage chamber 208 for immediate use during the procedure.

Figure 16:
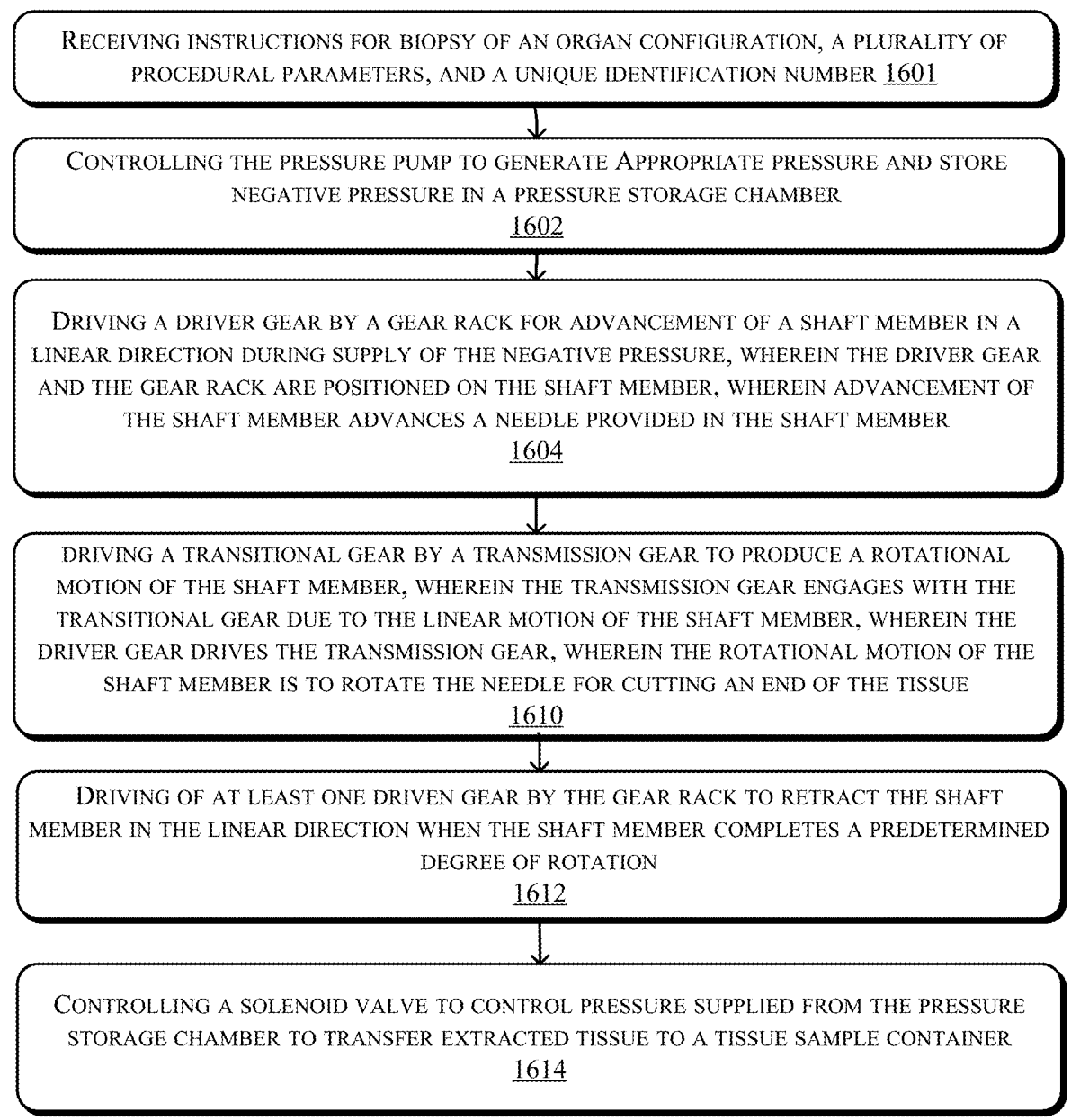
FIG. 16 illustrates a method for performing biopsy, according to an embodiment of the present subject matter.

The present subject matter also provides a method for performing biopsy. For the sake of convenience and ease of understanding, the method 1600 as illustrated in FIG. 16 has been explained with respect to FIGS. 1-15. The order in which the method 1600 is described is not intended to be construed as a limitation, and any number of the described method blocks may be combined in any order to implement the method 1600, or alternative methods.

At block 1601, instruction for biopsy of an organ configuration, a plurality of biopsy parameters and a unique identification number are received. In an embodiment, the instructions are received by the control subsystem 116. At block 1602, a pressure pump is controlled to generate and store negative pressure in a pressure storage chamber. In an embodiment, the pressure pump and the pressure storage chamber are pressure pump 204 and pressure storage chamber 208, respectively.

In an embodiment, as explained previously, needle 414 is inserted into the patient's body up to a surface the organ being biopsied based on predetermined length as fixed by the needle depth adjuster 218. In an embodiment, the circular disc of the needle depth adjuster 218 rests externally on the patient's skin to provide a stable operation of the biopsy device 100. Further, data from user interface 1416 and stopper switch 1402 can be received, for example, by to control subsystem 116 indicating whether the needle depth adjuster device 218 has been pressed against the patient.

At block 1604, upon receiving instructions from a user interface, for example, user interface 1416 and confirming the status of the stopper switch, the negative pressure stored in the pressure storage chamber 208 is supplied to a needle to extract tissue from the organ and a driver gear is driven by a gear rack, for advancement of a shaft member in a linear direction during supply of the negative pressure. In an embodiment, the driver gear, gear rack, and shaft member are driver gear 404, gear rack 402, and shaft member 412 respectively. As explained previously, the driver gear 404 and the gear rack 402 are positioned on the shaft member 412. Advancement of the shaft member 412 advances a needle provided in the shaft member 412. In an embodiment, the needle is 414.

Once the tissue has been extracted in the needle 414, the advancement of the needle 414 is stopped. The supply of negative pressure to the needle 414 is also stopped.

At block 1610, a transitional gear is continued to be driven by a transmission gear to produce a rotational motion of the shaft member. In an embodiment, the transitional gear and transmission gear are transitional gear 416 and transmission gear 406, respectively. The transmission gear 406 engages with the transitional gear 412 due to the linear motion of the shaft member 412. The driver gear 404 drives the transmission gear 406. The rotational motion of the shaft member 412 is to rotate the needle for cutting an end of the tissue.

At block 1612, at least one driven gear is driven by the gear rack to retract the shaft member in the linear direction when the shaft member completes a predetermined degree of rotation. Retraction of the shaft member causes retraction of the needle. This further helps in avoiding any injuries that may be caused due to needle pricks. In an embodiment, the at least one driven gear is driven gear 410.

At block 1614, a solenoid valve is controlled to control pressure supplied from the pressure storage chamber. The supplied pressure transfers extracted tissue to a tissue sample container. In an embodiment, the tissue sample container is tissue sample container 110.

The present subject matter provides an automated, portable, and efficient biopsy device which is also easy to handle while minimalizing the possibility of surgical complications occurring during biopsy. The biopsy device also provides precise and controlled needle insertion which ensures good quality of tissue for subsequent studies while also reducing chances of damage or injury caused due to improper tissue extraction.

Although the subject matter has been described in considerable detail with reference to certain examples and implementations thereof, other implementations are possible. As such, the scope of the present subject matter is not limited to the description of the preferred examples and implementations contained therein.

What is claimed is:

1. A device for biopsy, the device comprising:
    a probe unit comprising:
        an injection unit comprising a needle for biopsy; and
        a driving mechanism for actuation of the injection unit, the driving mechanism comprising:
            a shaft member, wherein the needle is fixedly attached in the shaft member;
            a driver gear positioned on the shaft member;
            a gear rack positioned on the shaft member, wherein the driver gear is engaged with the gear rack, wherein the driver gear is to drive the gear rack to advance the shaft member in a linear direction;
            a transitional gear positioned at a proximal end of the shaft member;
            a transmission gear positioned on the shaft member, wherein the driver gear engages with the transmission gear to drive the transitional gear, wherein the transmission gear is to drive the transitional gear to produce a rotational motion of the shaft member;
            at least one driven gear positioned on the shaft member, wherein when the shaft member completes a rotation by a predetermined angle the gear rack is to engage with and drive the at least one driven gear to retract the shaft member in the linear direction; and
    a driver unit, wherein the driving mechanism of the probe unit is coupled to the driver unit, the driver unit comprising:
        a prime-mover, wherein the prime-mover is for actuation of the needle by actuating the driving mechanism for bi-directional sequential movement of advancing, retracting, and rotating the needle;
        a pressure subsystem, wherein the pressure subsystem is coupled to the probe unit, the pressure subsystem comprising:
            a pressure pump to supply negative pressure to the probe unit for biopsy; and
            a pressure storage chamber to store pressure supplied by the pressure pump for instantaneous application of pressure at the time of procedure; and
        a control subsystem to control the pressure subsystem to provide varying pressure for biopsy.

2. The device as claimed in claim 1, wherein the pressure subsystem comprises:
    a check valve coupled between the pressure storage chamber and the pressure pump, wherein the check valve is to prevent reverse flow of the pressure stored in the pressure storage chamber;
    a solenoid valve coupled to the pressure storage chamber to control pressure provided by the pressure storage chamber to the probe unit; and
    an interfacing element to provide pressure from the pressure storage chamber to a filter chamber provided in a tissue sample container coupled to the probe unit.

3. The device as claimed in claim 2, wherein the tissue sample container is detachably coupled to the probe unit, wherein the tissue sample container comprises:
    an inlet opening to house a proximal end of the needle;
    a first compartment to receive tissue from the needle;
    a plate to separate the first compartment and a second compartment, wherein the plate is to allow seeping of fluids from the first compartment to second compartment;

the second compartment, wherein the second compartment comprises conduits to couple to the filter chamber; and
a Near Frequency Communication (NFC) tag to identify the tissue sample container.

4. The device as claimed in claim 1, wherein the device comprises a needle depth adjuster comprising:
a circular disc at a first end of the needle depth adjuster; and
a locking arm at a second end of the needle depth adjuster, wherein the locking arm is to lock the driver unit at a locking position and to control a length of the needle, wherein the locking arm comprises:
a magnet, wherein the length of the needle is detected based on a position of the magnet by a plurality of magnet sensors in the driver unit.

5. The device as claimed in claim 1, wherein the device comprises a needle depth adjuster coupled to a distal end of the injection unit, wherein the needle depth adjuster is extendable and lockable to prevent or limit undesired length of needle insertion, wherein the needle depth adjuster comprises:
an aligning unit for aligning the device with an external device;
a central part for locking with the driver unit; and
a semi-circular flap coupled to the central part, wherein the semi-circular flap has an open-close configuration, wherein the semi-circular flap is closed during biopsy.

6. A device for biopsy, the device comprising:
a probe unit comprising:
an injection unit comprising a needle for biopsy; and
a driving mechanism for actuation of the injection unit, the driving mechanism comprising:
a shaft member, wherein the needle is fixedly attached in the shaft member wherein the driving mechanism is to advance the shaft member and retract the shaft member in a linear direction and to produce a rotational motion of the shaft member; and
a driver unit, wherein the driving mechanism of the probe unit is coupled to the driver unit, the driver unit comprising:
a prime-mover, wherein the prime-mover is for actuation of the needle by actuating the driving mechanism for bi-directional sequential movement of advancing, retracting, and rotating the needle;
a pressure subsystem, wherein the pressure subsystem is coupled to the probe unit, the pressure subsystem comprising:
a pressure pump to supply negative pressure to the probe unit for biopsy; and
a pressure storage chamber to store pressure supplied by the pressure pump for instantaneous application of pressure at the time of procedure; and
a control subsystem to control the pressure subsystem to provide varying pressure for biopsy;
wherein the pressure subsystem comprises:
a check valve coupled between the pressure storage chamber and the pressure pump, wherein the check valve is to prevent reverse flow of the pressure stored in the pressure storage chamber;
a solenoid valve coupled to the pressure storage chamber to control pressure provided by the pressure storage chamber to the probe unit; and
an interfacing element to provide pressure from the pressure storage chamber to a filter chamber provided in a tissue sample container coupled to the probe unit, and wherein the filter chamber is coupled to the interfacing member via conduits, wherein the filter chamber comprises:
a primary chamber and secondary chamber;
a plurality of filter members stacked one above the other in the filter chamber; and
empty spaces comprising a hydrogel pad to absorb fluid impurities, wherein on application of negative pressure through the filter chamber (208):
the filter chamber is to absorb impurities from the tissue sample in the tissue sample container;
the plurality of filter members is to blot absorbed impurities;
the empty spaces are to drain residual fluid impurities.

7. A device for biopsy, the device comprising:
a probe unit comprising:
an injection unit comprising a needle for biopsy; and
a driving mechanism for actuation of the injection unit, the driving mechanism comprising:
a shaft member, wherein the needle is fixedly attached in the shaft member, wherein the driving mechanism is to advance the shaft member and retract the shaft member in a linear direction and to produce a rotational motion of the shaft member; and
a driver unit, wherein the driving mechanism of the probe unit is coupled to the driver unit, the driver unit comprising:
a prime-mover, wherein the prime-mover is for actuation of the needle by actuating the driving mechanism for bi-directional sequential movement of advancing, retracting, and rotating the needle;
a pressure subsystem, wherein the pressure subsystem is coupled to the probe unit, the pressure subsystem comprising:
a pressure pump to supply negative pressure to the probe unit for biopsy; and
a pressure storage chamber to store pressure supplied by the pressure pump for instantaneous application of pressure at the time of procedure; and
a control subsystem to control the pressure subsystem to provide varying pressure for biopsy;
wherein the control subsystem is configured to:
issue command to the pressure pump to generate a partial vacuum in the pressure storage chamber;
receive signals from a plurality of pressure sensors in the pressure subsystem and based on the signals, the control subsystem is configured to control:
a solenoid valve to control pressure provided to the probe unit; and
a check valve to prevent reverse flow of pressure;
the prime-mover to actuate the driving mechanism; and
receive status of the probe unit, wherein the status comprises a lock position of the probe unit;
receive a length of the needle from the Hall sensors.

8. A method of performing biopsy, the method comprising:
receiving instructions for biopsy of an organ configuration, a plurality of procedural parameters, and a unique identification number;
controlling a pressure pump to generate appropriate pressure and store negative pressure in a pressure storage chamber;
inserting a needle into a patient up to the organ surface based on a predetermined length as fixed by a needle depth adjuster;
upon receiving instructions from a user interface and confirming the status of a stopper switch, supplying the negative pressure stored in the pressure storage chamber to a needle to extract tissue from the organ;

driving a driver gear by a gear rack for advancement of a shaft member in a linear direction during supply of the negative pressure, wherein the driver gear and the gear rack are positioned on the shaft member, wherein advancement of the shaft member advances the needle provided in the shaft member;

stopping advancement of the needle and supply of the negative pressure to the needle;

continuing driving a transitional gear by a transmission gear to produce a rotational motion of the shaft member, wherein the transmission gear engages with the transitional gear due to the linear motion of the shaft member, wherein the driver gear drives the transmission gear, wherein the rotational motion of the shaft member rotates the needle for cutting an end of the tissue;

driving of at least one driven gear by the gear rack to retract the shaft member in the linear direction to avoid any needle prick injuries when the shaft member completes a predetermined degree of rotation; and controlling a solenoid valve to control negative pressure supplied from the pressure storage chamber to transfer extracted tissue to a tissue sample container or positive pressure to transfer extracted tissue into an external container.

\* \* \* \* \*